United States Patent [19]
Reed

[11] Patent Number: 5,854,049
[45] Date of Patent: Dec. 29, 1998

[54] PLASMIN-RESISTANT STREPTOKINASE

[75] Inventor: Guy L. Reed, Winchester, Mass.

[73] Assignee: President and Fellows of Harvard College, Cambridge, Mass.

[21] Appl. No.: 488,940

[22] Filed: Jun. 9, 1995

[51] Int. Cl.$^6$ .............................. C12N 9/70; C12P 21/04; A61K 35/14; C07K 1/00
[52] U.S. Cl. ........................ 435/216; 435/69.6; 435/69.7; 530/380
[58] Field of Search .................................. 435/216, 69.6, 435/69.7; 530/380

[56] References Cited

U.S. PATENT DOCUMENTS

| | | | |
|---|---|---|---|
| 5,011,686 | 4/1991 | Pang ........................................ | 424/94.1 |
| 5,187,098 | 2/1993 | Malke et al. .......................... | 435/320.1 |
| 5,434,073 | 7/1995 | Dawson et al. .......................... | 435/216 |

FOREIGN PATENT DOCUMENTS

| | | |
|---|---|---|
| WO 91/09125 | 6/1991 | WIPO . |
| WO94/07992 | 4/1994 | WIPO . |

OTHER PUBLICATIONS

Klessen et al., "Tripartite Streptokinase Gene Fusion Vectors for Gram–Positive and Gram–Negative Procaryotes", *Mol. Gen. Genet.*, 212:295–300 (1988).

Lin et al., "Mutational Studies of Streptokinase Identify Amino Acid Residues Critical to Generation of a Functional SK–Plasminogen Activator Complex", Abstracts From the 68th Scientific Sessions, Anaheim, CA, USA, Nov. 13–16, 1995, Circulation 92 (8 Supp), I–623, No. 2984.

Liu et al., "Recombinant Streptokinases Resistant to Cleavage and Inactivation by Plasmin", Abstracts From the 68th Scientific Sessions, Anaheim, CA, USA, Nov. 13–16, 1995, Circulation 92 (8 Supp), I–623, No. 2985.

Buck et al., "Interaction of Streptokinase and Human Plasminogen," *J. Biol. Chem.*, 246(7):2091–2096 (1971).

Davidson et al., "Plasminogen Activator Activities of Equimolar Complexes of Streptokinase with Variant Recombinant Plasminogens," *Biochemistry*, 29:3585–90 (1990).

Ferres, "Preclinical Pharmacological Evaluation of Anisoylated Plasminogen Streptokinase Activator Complex," *Drugs*, 33(Suppl. 3), 33–50 (1987).

Lee et al., "Site–Specific Alteration of Gly–24 in Streptokinase: Its Effect on Plasminogen Activation", *Biochemical and Biophysical Research Communications*, 165:1085–90, (1989).

Malke et al., "Nucleotide Sequence of the Streptokinase Gene from Streptococcus Equisimilis H46A," *Gene*, 34:357–362 (1985).

Markus et al., "Activator Activities of the Transient Forms of the Human Plasminogen Streptokinase Complex during Its Proteolytic Conversion to the Stable Activator Complex," *J. Biol. Chem.*, 251(21):6495–6504 (1976).

Rajagopalan et al., "A Nonantigenic Covalent Streptokinase—Polyethylene Glycol Complex with Plasminogen Activator Function," *J. Clin. Invest.*, 75:413–419 (1985).

Reddy, "Streptokinase—Biochemistry and Clinical Application," *Enzyme*, 40:79–89 (1988).

Reed et al., "A Functional Analysis of the Antigenicity of Streptokinase Using Monoclonal Antibody Mapping and Recombinant Streptokinase Fragments," *J. of Immun.*, 150(10):4407–15 (1993).

Reed et al., "Studies with Recombinant Streptokinase Fragments Indicate That Binding Is Not Sufficient for a Functional Streptokinase–Plasminogen Activator Complex", *Circulation*, 88:I–615; No. 3310, Nov. 8–11, 1993.

Robbins, "The Plasminogen—Plasmin Enzyme System," *Fibrinolysis*, Chapter 21, 340–357 (1987).

Sadowski, "Bacteriophage T7 Endonuclease I: Properties of the Enzyme Purified from T7 Phage–Infected *Escherichia Coli* B", *J. of Biol. Chem.* 246(1):209–216 (1971).

Siefring et al., "Interaction of Streptokinase with Plasminogen," *J. Biol. Chem.*, 251(13):3913–20 (1976).

Staniforth et al., "Streptokinase and Anisoylated Streptokinase Plasminogen Complex," *Eur J. Clin Pharmacol.*, 24:751–756 (1983).

*Primary Examiner*—Robert A. Wax
*Assistant Examiner*—Lisa J. Hobbs
*Attorney, Agent, or Firm*—Fish & Richardson P.C.

[57] ABSTRACT

The invention features modified streptokinase (SK) molecules which are resistant to plasmin cleavage including a recombinant fusion protein in which the amino terminus of SK was blocked with a peptide, a recombinant fusion protein in which an amino-terminal deleted SK was blocked with a peptide, and a mutated SK in which plasmin-cleavage sites were altered to render those sites resistant to enzymatic cleavage.

8 Claims, 7 Drawing Sheets

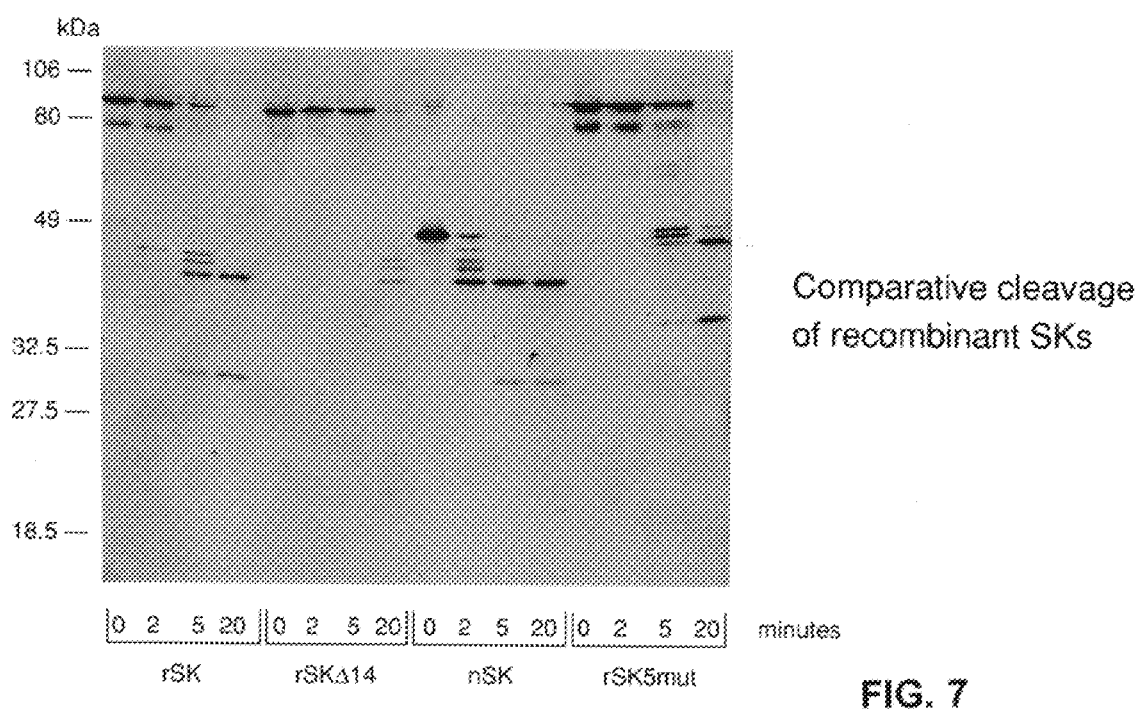
FIG. 7 Comparative cleavage of recombinant SKs

PLASMIN-RESISTANT STREPTOKINASE

This invention is supported by NIH Grant No. HL02348, U.S. Government therefore has certain rights in the invention.

BACKGROUND OF THE INVENTION

Streptokinase (SK), isolated from Group C streptococcus, is used as a plasminogen activator to accelerate the lysis of the coronary thrombi that cause heart attacks. However, SK is by itself inert and must combine with human plasminogen to form a catalytically-active SK-plasminogen activator complex (SK-PAC) which cleaves substrate plasminogen molecules. Studies of proteolytic fragments of SK and recombinant truncation mutants have defined regions of SK which are important for binding interactions with plasminogen in the construction of the activator complex. Through undefined molecular interactions, an active site appears in the plasminogen moiety of the SK-PAC (Buck et al., 1968, J. Biol. Chem. 246:209–246). The SK-PAC then generates the active enzyme plasmin by clipping substrate plasminogen molecules at the Arg560-Val bond (Robbins et al., 1987, In Colman et al., Hemostasis and thrombosis: basic principles and clinical practice, 2nd ed., Lippincott, Pa., pp. 341–357).

Almost immediately after forming an active SK-PAC, the SK moiety is clipped to smaller molecular weight forms (Siefring and Castellino, 1976, J. Biol. Chem. 251:3913–3920; Markus et al., 1976, J. Biol. Chem. 251:6495–6504). Cleavage of SK markedly reduces the catalytic activity of the activator complex (Markus et al., 1976, supra). Enzymatic studies of SK fragments isolated after reacting with plasminogen at lower temperatures suggests that SK activity declines with progressive cleavage (Markus et al., 1976, supra).

Inactivation of SK in plasma as a result of plasmin cleavage reduces the therapeutic effectiveness of this plasminogen activation.

SUMMARY OF THE INVENTION

The SK-derived compounds of the invention resist cleavage inactivation by plasmin, while retaining all or a substantial portion of the plasminogen-binding and catalytic activity of native SK. SK modified according to the invention is a more potent thrombolytic agent than native SK, and therefore, is a more useful therapeutic tool.

The invention features a compound containing (a) a plasminogen-binding fragment of SK and (b) a blocking group at the amino-terminus of the fragment. By the term "streptokinase" is meant an indirect plasminogen activator derived from streptococci. By the term "fragment" is meant a polypeptide containing less than or all of the native, full-length amino acid sequence of SK. SK may be recombinant or purified from streptococci, and the streptococci from which it is derived is preferably β-hemolytic. Alternatively, the streptokinase may be derived from an α-hemolytic streptococci. The streptococci from which SK is derived is preferably from Group C, e.g., *Streptococcus equisimilus,* however SK may also be derived from streptococci of Group A or Group G.

The compound is catalytically active and the rate of in vitro degradation in the presence of human plasminogen is at least two times slower than the rate of native, full-length mature SK protein derived from *Streptococcus equisimilus* (nSK), i.e., the time required from the addition of SK to plasminogen to the disappearance of the band on a Western blot corresponding to the uncleaved nSK. For example, the time required for the disappearance of uncleaved nSK is about 2 min., whereas the time for the disappearance of modified SK ranges from 7 min. to greater than 20 min. By the term "catalytically active" is meant it possesses the ability of SK to interact with plasminogen to form a SK-PAC capable of activating plasminogen to plasmin. By the term "degradation" is meant the process by which SK is reduced by plasmin cleavage into lower molecular weight fragments. The rate of degradation is measured by the disappearance of a full-length recombinant SK as detected by immunoblotting using anti-SK antibodies.

The compound preferably contains the amino acid sequence of SEQ ID NO:4. The blocking group of the compound may be a peptide or a non-peptide blocking group which is located at the amino-terminus of the SK fragment. For example, a blocking group may be introduced by glycosylation or myristolization. Preferably, the blocking group is least one heterologous amino acid; more preferably, the blocking group is a heterologous peptide of two or more amino acids; and most preferably, the blocking group is a fragment of or all of maltose binding protein (MBP). By the term "heterologous" is meant an addition or substitution of one or more amino acids that is different from that found at the corresponding site in nSK.

The invention also includes a DNA, e.g., a DNA vector, containing a coding sequence which encodes the polypeptide portion of the compound of the invention, and a method of dissolving blood clots in a mammal by administering an effective amount of the compound. An effective amount of the compound is an amount which is effective in dissolving at least one blood clot in a patient.

The invention also features a plasminogen-binding fragment of SK which is catalytically active and the rate of in vitro degradation of which is at least two times slower than the rate of nSK in the presence of human plasminogen. The fragment preferably comprises at least 95% of the amino acid sequence of nSK; more preferably, the fragment lacks one to five amino-terminal amino acids of nSK; more preferably, the fragment lacks one to ten amino-terminal amino acids; more preferably, the fragment lacks 1–24 amino acids. In a preferred embodiment, the fragment consists of amino acids 14–414 of nSK (SEQ ID NO:4). A fragment consisting of amino acids 14–414 of nSK (SEQ ID NO:4) may also contain at least one or more mutations selected from the group consisting of K36A, R45A, K51A, K59A, K61A, K147A, K333, R232A, K257A, K298A, K309A, R234A, R363A, K386A, K372A, R388A, R394A, and R401A.

The invention also includes an SK polypeptide which is catalytically active and the rate of in vitro degradation of which is at least two times slower compared to the rate of nSK. By "polypeptide" is meant a chain of amino acids, regardless of length or post-translational modification (e.g., glycosylation or phosphorylation). Preferably, the polypeptide consists of the amino acid sequence of nSK in which at least one potential plasmin cleavage site has been mutated to render it resistant to plasmin cleavage. More preferably, the polypeptide contains one or more mutations selected from the group consisting of R10A, K36A, R45A, K51A, K59A, K61A, K147A, K333, R232A, K257A, K298A, K309A, R234A, R363A, K386A, K372A, R388A, R394A, and R401A. Most preferably, the fragment is rSK5mut (SEQ ID NO:17), which contains the mutations, R10A, R36A, R45A, R51A, and R59A or rSK6mut, which contains the mutations R10A, R36A, R45A, R51A, R59A, and K386A (SEQ ID NO:18). The invention also includes a DNA containing a coding sequence encoding the SK polypeptide of the invention and a method of dissolving blood clots in a mammal by administering to the mammal an effective amount of the SK polypeptide of the invention.

Other features and advantages of the invention will be apparent from the following description of the preferred embodiments thereof, and from the claims.

DETAILED DESCRIPTION

The drawings will first be described.

Drawings

FIG. 7 is a photograph of a Western blot showing comparative plasmin cleavage of rSK, rSKΔ14, nSK, and rSK5mut.

MODIFICATION OF SK TO RENDER IT RESISTANT TO DEGRADATION BY PLASMIN

Figure 1:
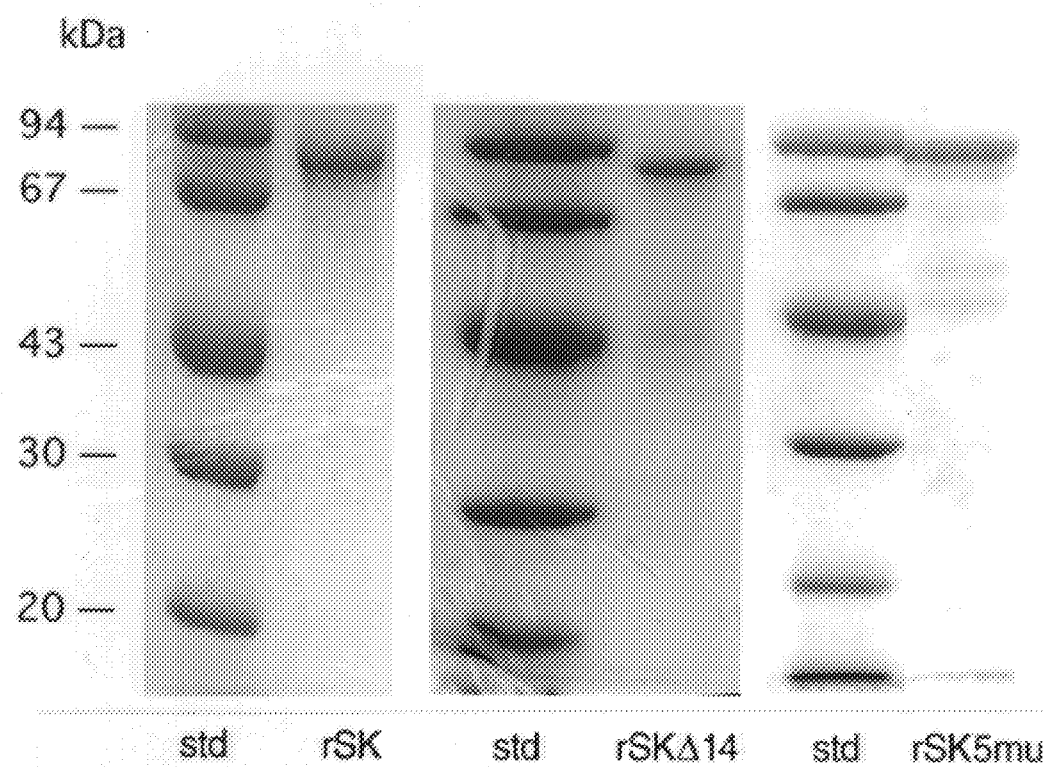
FIG. 1 is a photograph of a Western blot showing purification of a fusion protein with maltose binding protein linked to the amino terminus nSK (rSK), a fusion protein with MBP linked to the amino terminus of nSK in which the amino terminal 13 amino acids of nSK were deleted (rSKΔ14), and rSK5mut.

Within seconds, binding of SK to plasminogen to form SK-PAC, nSK is rapidly degraded at its amino terminus by plasmin. Through the process of degradation, plasmin limits the thrombolytic efficacy of nSK. According to the invention, SK can be modified in three different ways to render it resistant to plasmin cleavage: (1) by blocking the amino terminus of nSK, e.g., with a heterologous peptide; (2) by deleting one or more amino terminal amino acids from nSK; and (3) by altering plasmin cleavage sites throughout nSK to render them resistant to plasmin cleavage.

In one example, a recombinant fusion protein was made in which the amino terminus of nSK was tethered in peptide linkage to MBP (rSK). In another example, a recombinant fusion protein was made in which the MBP was linked to the amino terminus of nSK, the first 13 amino acids of which were deleted. In the third example, the nSK amino acid sequence was mutated at plasmin-cleavage sites to render those sites resistant to enzymatic cleavage, e.g., in the mutant rSK5mut, the K or R residue in five potential plasmin cleavage sites were changed to A residues. In each case, plasmin cleavage yielded catalytically active plasmin cleavage products, but the rate of degradation was markedly reduced compared to that of nSK. In addition to affecting the rate of degradation, mutation of plasmin cleavage sites also significantly decreases the $K_m$ of amidolytic activity, which leads to greater catalytic efficiency.

Therapeutic Applications

The compounds of the invention can be used to lyse blood clots in a mammal. The compounds can be administered by any standard route including intraperitoneally, intramuscularly, subcutaneously, or intravenously. It is expected that the preferred route of administration will be intravenous. The compounds can be administered systemically to the bloodstream as well as locally within the blood vessel at the site of clot formation. Since the compounds of the invention are timed-release, they can be administered in a single dose rather than by continuous infusion.

As is well known in the medical arts, dosages for any one patient depends on many factors, including the patients general health, sex, size, body surface area, age, as well as the particular compound to be administered, time and route of administration, and other drugs being administered concurrently. Dosages for the compounds of the invention will vary, but a preferred dosage for administration to human patients is approximately 20,000 units per kg of body weight (units of SK are defined in Bulletin. World. Health. Org., 1965, 33:235). Determination of correct dosage for a given application is well within the abilities of one of ordinary skill in the art of pharmacology. Optimal dosage may be adjusted according to the condition of the patient and response of the patient to therapy.

EXAMPLE 1

Modification of the amino terminus of streptokinase modulates the appearance of the active site in the SK-PAC To examine the functional role of the amino terminus of SK in the SK-PAC, the amino terminus of SK was recombinantly modified by partial deletion of amino-terminal amino acids or by tethering of the amino terminus with a blocking group, e.g., a heterologous peptide. Functional activity of the modified SK was evaluated by measuring (1) the rate of plasminogen activation by SK-PAC, (2) the amidolytic activity of the SK-PAC, and (3) the plasmin-mediated degradation of SK in the SK-PAC.

Cloning, Expression and Purification of Streptokinase

The SK gene (Malke et al., 1985, Gene 34:357–362) was cloned from *Streptococcus equisimilis* by the polymerase chain reaction (PCR), sequenced (U.S. Biochemicals, Cleveland, Ohio; Sanger et al., 1977, Proc. Natl. Acad. Sci U.S.A. 74:5463) and subcloned into the pMAL vector for bacterial expression (New England Biolabs, Beverly, Mass.) using known methods, e.g., Reed et al., 1993, J. Immunol. 150:4407–4415; Reed et al., 1993, Circulation 88:Abstract I-615). The expressed SK gene formed a fusion protein with maltose binding protein at its amino terminus (rSK). Restriction digestion of the SK gene with Hinc II removed the nucleotides encoding the amino terminal 13 amino acids of SK to produce deletion mutant, rSKΔ14. These recombinant SK fusion proteins were purified by affinity chromatography on an amylose resin (New England Biolabs, Beverly, Mass.) as described by the supplier. The purity of the recombinant SK fusion proteins was assessed by SDS-PAGE (Laemmli, 1970, Nature 227:680–685). For some experiments, the SK fusion proteins were cut with factor Xa (Maina et al., 1988, Gene 74:365) and the MBP portion of the fusion protein removed by affinity chromatography on an amylose resin.

After purification, the relative concentrations of the recombinant SKs were determined by comparative radioimmunoassay (RIA) using anti-SK monoclonal antibodies. Wells of a microtiter plate were coated with various concentrations of nSK (0, 2.5, 5, 10, 20, and 40 μg/mL) or different dilutions of the recombinant SKs, rSKΔ14 and rSK5mut. After nonspecific binding sites had been blocked with 1% bovine serum albumin, anti-SK monoclonal antibodies were added to each well in duplicate. After a 1-h incubation, the wells were washed and probed with $^{125}$I goat anti-mouse antibody (Cappel Organon Teknika, Durham, N.C.) for 1 h. After another wash, the amount of bound antibody was determined by gamma counting. A standard curve relating antibody binding (cpm) to nSK concentration was derived and the concentration of each recombinant SK was determined by reference to the standard curve.

Plasminogen Activation by recombinant SKs

Studies of the time-related activity of different SKs were carried out by mixing Glu-plasminogen (333 nM; American Diagnostica, Greenwich, CT) in a quartz cuvette with S2251 (0.5 mM; H-D-valyl-L-leucyl-L-lysine-p-nitroanilide dihydrochloride, Chromogenix, Sweden) at 21° C. or 37° C. and then adding purified nSK, rSK, or rSKΔ14 (16.7 nM). Absorption at 405 nanometers was continuously monitored in a Hewlett-Packard diode array spectrophotometer.

Active Site Titration

The development of an active site in the SK-PAC was monitored using standard methods. Plasminogen (8.5 μg; Sigma, St. Louis, Mo.) was added to a quartz cuvette containing 2 ml of filtered buffer (50 mM, 100 mM NaCl, pH 7.4) and 1 mM of the fluorogenic substrate 4-methylumbelliferyl p-guanidinobenzoate (Sigma, St. Louis, Mo.) thermostatically maintained at 25° C. The emission at 445 nanometers (excitation at 365 nanometers) was continuously monitored in a Hitachi 2000 fluorescence spectrophotometer. After ~200 seconds of observation, rSK was added, and the reaction was recorded for a total of 2000 seconds.

Kinetic Assays of the SK-PAC

The amidase kinetic parameters of nSK, rSK and rSKΔ14 were studied using a paranitroanilide substrate (S2251, H-D-valyl-L-leucyl-L-lysine-p-nitroanilide dihydrochloride, Chromogenix, Sweden) using known methods, e.g., Wohl R. et al., 1980., Biochim. et Biophys. Acta 745:20–31). The recombinant SK proteins and Glu-plasminogen were mixed together and incubated for 5 min. (nSK and rSK) or 20 min (rSKΔ14) at 37° C. The mixture was then transferred to a quartz cuvette containing assay buffer (50 mM Tris, 100 mM NaCl, pH 7.4) and various concentrations of S2251 (100–800 μM) added. The cuvette was thermostatically regulated at 37° C. The change in absorbance was monitored at 404 nM for 10 min. at 37° C., and the data were transformed to Linewaever-Burke plots to determine the $K_m$ and $V_{max}$.

Studies of the degradation of SK by plasmin

The time-related proteolysis of nSK, rSK, rSKΔ14, and rSK5mut was studied by immunoblotting. nSK (1 μg) or recombinant SKs (2 μg) were mixed together with purified human Glu-plasminogen (40 μgs; American Diagnositica, 98% Glu-type plasminogen) for 0–20 min. The amount of human plasminogen present is typically in excess of the amount of SK. At various time points, an aliquot (5 μl) was removed and plunged into boiling water to stop the reaction. The samples were then electrophoresed on 10% SDS-polyacrylamide under reducing conditions and electrophoretically transferred to polyvinylidene difluoride membranes (Millipore, Bedford, Mass.). Nonspecific binding sites were blocked with 5% nonfat milk for 1 hr. The blots were incubated with pooled monoclonal antibodies specific for SK overnight at 4° C. The blots were washed and incubated for 1 hr. with $^{125}$I-goat antimouse antibody (~1,000,000 cpm; Cappel Organon Teknika, Durham, N.C.) which had been labelled using the Iodogen labelling method known in the art. After washing, the blots were exposed to Kodak X-O-mat film (Rochester, N.Y.) at −70° C.

Amino-terminal modification of SK

SK was produced as a fusion protein with MBP at its amino terminus (rSK), the amino acid sequence of which is shown in Table 1. A mutant lacking the first 13 amino acids of SK was also produced as a fusion protein (rSKΔ14), the amino acid sequence of which is shown in Table 2. The amino acid sequence of nSK is shown in Table 3, and the amino acid sequence of SKΔ14 is shown in Table 4. The sequence of both rSK and rSKΔ14 suggested that they could be cleaved at the fusion protein junction by factor Xa. The production of the rSK proteins in E. coli was induced by IPTG. Recombinant SK proteins were purified from bacterial lysates by affinity chromatography. As shown in FIG. 1, the proteins migrated at the predicted molecular size (rSK: 89 kDa, rSKΔ14: 87 kDa).

TABLE 1 rSK

M K T E E G K L V I W I N G D K G Y N G L A E V G K K F E K D T G I K V T V E H P D K L E E K F P Q V A A T G D G P D I
I F W A H D R F G G Y A Q S G L L A E I T P D K A F Q D K L Y P F T W D A V R Y N G K L I A Y P I A V E A L S L I Y N K
D L L P N P P K T W E E I P A L D K E L K A K G K S A L M F N L Q E P Y F T W P L I A A P G G Y A F K Y E N G K Y D I K
D V G V D N A G A K A G L T F L V D L I K N K H M N A D T D Y S I A E A A F N K G E T A M T I N G P W A W S N I D T S K
V N Y G V T V L P T F K G Q P S K P F V G V L S A G I N A A S P N K E L A K E F L E N Y L L T D E G L E A V N K D K P L
G A V A L K S Y E E E L A K D P R I A A T M E N A Q K G E I M P N I P Q M S A F W Y A V R T A V I N A A S G R Q T V D E
A L K D A Q T N S S S V P G R G S I E G R I A G P E W L L D R P S V N N S Q L V V S V A G T V E G T N Q D I S L K F F E
I D L T S R P A H G G K T E Q G L S P K S K P F A T D S G A M S H K L E K A D L L K A I Q E Q L I A N V H S N D D Y F E
V I D F A S D A T I T D R N G K V Y F A D K D G S V T L P T Q P V Q E F L L S G H V R V R Y K E K P I Q N Q A K S V D V
E Y T V Q F T P L N P D D D F R P G L K D T K L L K T L A I G D T I T S Q E L L A Q A Q S I L N K N H P G Y T I Y E R D
S S I V T H D N D I F R T I L P M D Q E F T Y R V I (N R E Q A Y R I N K K S G L N E E I N N T D L I S E K Y Y V L K K G
E K P Y D P F D R S H L K L F T I K Y V D V D T N E L L K S E Q L L T A S E R N L D F R D L Y D P R D K A K L L Y N N L
D A F G I M D Y T L T G K V E D N H D D T N R I I T V Y M G K R P E G E N A S Y H L A Y D K D R Y T E E E R E V Y S Y L
R Y T G T P I P D N P N D K N N S Q L V V S V A G T V E G T N Q D I S L K F F E I D L T S R P A H G G K T E Q G L S P K
S K P F A T D S G A M S H K L E K A D L L K A I Q E Q L I A N V H S N D D Y F E V I D F A S D A T I T D R N G K V Y F
A D K D G S V T L P T Q P V Q E F L L S G H V R V R Y K E K P I Q N Q A K S V D V E Y T V Q F T P L N P D D D F R P G L
K D T K L L K T L A I G D T I T S Q E L L A Q A Q S I L N K N H P G Y T I Y E R D S S I V T H D N D I F R T I L P M D Q
E F T Y R V K N R E Q A Y R I N K K S G L N E E I N N T D L I S E K Y Y V L K K G E K P Y D P F D R S H L K L F T I K Y
V D V D T N E L L K S E Q L L T A S E R N L D F R D L Y D P R D K A K L L Y N N L D A F G I M D Y T L T G K V E D N H D
D T N R I I T V Y M G K R P E G E N A S Y H L A Y D K D R Y T E E E R E V Y S Y L R Y T G T P I P D N P N D K (SEQ ID NO: 1)

TABLE 2 rSKΔ14

MKTEEGKLVI WI NGDKGYNGLAE VGKKF EKDTGI KVTVEHP DKLEE KFP QVAATGDGP DI
I F WAHDRF GGYAQS GLLAEI TP DKAF QDKL YP F TWDAVR YNGKLI AYP I AVEALS LI YNK
DLLP NP P KT WE EI P ALDKE L KAKGKS AL MF NL QE P YF T WP LI AADGGYAF KYENGKYDI K
DVGVDNAGAKAGL TF LVDLI KNKHMNADTDYS I AEAAF NKGE TAMTI NGP WAWS NI DTS K
VNYGVT VLP TF KGQP S KP F VGVLS AGZNAAS P NKELAKE F LE NYLLT DE GLE AVNKDKP L
GAVALKS YEE E LAKDP RI AATMENAQKGEI MP NI P QMS AF WYAVRTAVI NAAS GR QT VDE
ALKDAQT NS S S VP GRGS I EGRNNS QL VVS VAGT VE GT NQDI S LKF F EI DLTS RP AHGGKT
EQGLS P KS KP F ATDS GAMS HKLE KADLL KAI QE QLI ANVHS NDDYF E VI DF AS DATI TDR
NGKVYF ADKDGS VTLP T QP VQE F LLS GHVR VR YKE KP I QNQAKS VDVE YT VQF TP LNP DD
DF RP GLKDT KLL KT LAI GDTI TS QELLAQAQS I LNKNHP GYTI YERDS S I VTHDNDI F RT
I LP MDQE F TYR VKNRE QAYRI NKKS GLNEE I NNTDLI S E KYYVLKKGE KP YDP F DRS HLK
LF TI KYVDVDTNELLKS E QLLTAS E RNLDF RDL YDP RDKAKLL YNNLDAF GI MDYTLTGK
VEDNHDDT NRI I TVYMGKRP E GE NAS YHLAYDKDR YTE E E RE VYS YL RYTGTP I P DNP ND
KNNS QL VVS VAGT VE GT NQDI S LKF F EI DLTS RP AHGGKT E QGL S P KS KP F ATDS GAMS H
KLE KADLL KAI QE QLI AVVHS NDDYF E VI DF AS DATI TDRNGKVYF ADKDGS VTLP T QP V
QE F LLS GHVR VR YKE KP I QNQAKS VDVE YT VQF TP LNP DDDF RP GLKDT KLL KT LAI GDT
I TS QELLAQAQS I LNKNHP GYTI YERDS S I VTHDNDI F RTI LP MDQE F TYR VKNRE QAYR
I NKKS GLNEE I NNTDLI S E KYYVLKKGE KP YDP F DRS HLKLF TI KYVDVDTNELLKS E QL
LTAS E RNLDF RDL YDP RDKAKLL YNNLDAF GI MDYTLTGKVE DNHDDT NRI I TVYMGKR P
E GE NAS YHLAYDKDR YTE E E RE VYS YL RYTGTP I P DNP NDK (SEQ ID NO: 2)

TABLE 3 nSK

I AGP E WL L DRP S VNNS QL VVS VAGT VE GT NQDI S LKF F EI DLTS RP AHGGKTE QGL S P KS
KP F AT DS GAMS HKLE KADLL kAI QE QLI AVVHS NDDYF E VI DF AS DATI TDRNGKVYF AD
KDGS VTLP T QP VQE F LLS GHVR VR YKE KP I QNQAKS VDVE YT VQF TP LNP DDDF RP GLKD
T KLL KT LAI GDTI TS QELLAQAQS I LNKNHP GYTI YERDS S I VTHDNDI F RTI LP MDQE F
TYR VKNRE QAYRI NKKS GLNEE I NNTDLI S E KYYVLKKGE KP YDP F DRS HLKLF TI KYVD
VDT NELLKS E QLLTAS E RNLDF RDL YbP RDKAKLL YNNLDAF GI MDYTLTGKVE DNHDDT
NRI I TVYMGKRP E GE NAS YHLAYDKDR YTE E E RE VYS YL RYTGTP I P DNP NDKNNS QL VV
S VAGT VE GT NQDI S LKF F EI DLTS RP AHGGKT E QGL S P KS KP F ATDS GAMS HKLE KADLL
KAI QE QLI ANVHS NDDYF E VI DF AS DATI TDRNGKVYF ADKDGS VTLP T QP VQE F LLS GH
VR VR YKE KP I QNQAKS VDVE YT VQF TP LNP DDDF RP GLKDT KLL KT LAI GDTI TS QELLA
QAQS I LNKNHP GYTI YERDS S I VTHDNDI F RTI LP MDQE F TYR VKNRE QAYRI NKKS GLN
E EI NNTDLI S E KYYVLKKGE KP YDP F DRS HLKLF TI KYVDVDTNELLKS E QLLTAS E RNL
DF RDL YDP RDKAKLL YNNLDAF GI MDYTLTGKVE DNHDDT NRI I TVYMGKRP E GE NAS YH
LAYDKDR YTE E E RE VYS YL RYTGTP I P DNP NDK (SEQ ID NO: 3)

TABLE 4

SKΔ14

NNS QL VVS VAGT VE GT NQDI S LKF F EI DLTS RP AHGGKT E QGL S P KS KP F ATDS GAMS HK
LE KADLL KAI QE QLI ANVHS NDDYF E VI DF AS DATI TDRNGKVYF ADKDGS VTLP T QP VQ
E F LLS GHVR VR YKE KP I QNQAKS VDVE YT VQF TP LNP DDDF RP GLKDT KLL KT LAI GDTI
TS QELLAQAQS I LNKNHP GYTI YERDS S I VTHDNDI F RTI LP MDQE F TYR VKNRE QAYRI
NKKS GLNEE I NNTDLI S E KYYVLKKGE KP YDP F DRS HLKLF TI KYVDVDTNELLKS E QLL
TAS E RNLDF RDL YDP RDKAKLL YNNLDAF GI MDYTLTGKVE DNHDDT NRI I TVYMGKRP E
GE NAS YHLAYDKDR YTE E E RE VYS YL RYTGTP I P DNP NDKNNS QL VVS VAGT VE GT NQDI
S LKF F EI DLTS RP AHGGKT E QGL S P KS KP F ATDS GAMS HKLE KADLL KAI QE QLI ANVHS
NDDYF E VI DF AS DATI TDRNGKVYF ADKDGS VTLP T QP VQE F LLS GHVR VR YKE KP I QNQ
AKS VDVE YT VQF TP LNP DDDF RP GLKDT KLL KT LAI GDTI TS QELLAQAQS I LNKNHP GY
TI YERDS S I VTHDNDI F RTI LP MDQE F TYR VKNRE QAYRI NKKS GLNEE I NNTDLI S E KY
YVLKKGE KP YDP F DRS HLKLF TI KYVDVDTNELLKS E QLLTAS E RNLDF RDL YDP RDKAK
LL YNNLDAF GI MDYTLTGKVE DNHDDT NRI I TVYMGKRP E GE NAS YHLAYDKDR YTE E E R
E VYS YL RYTGTP I P DNP NDK (SEQ ID NO: 4)

Functional activity of recombinant SKs

Figure 2:
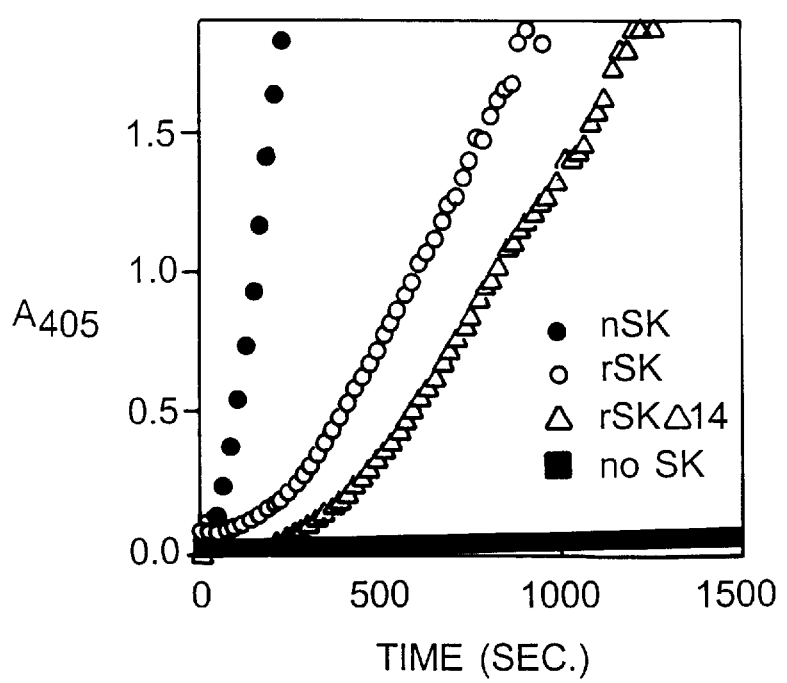
FIG. 2 is a graph showing plasminogen activation by nSK, rSK, and rSKΔ14.

To compare the function of SK, rSK and rSKΔ14, the rate of plasminogen activation by these proteins was examined at 21° C. nSK rapidly activated plasminogen with a minimal lag phase, i.e., less than 50 sec. (see FIG. 2). However, when expressed as a fusion protein, rSK showed a lag phase in plasminogen activation of approximately 150 sec. (see FIG. 2). When expressed as a fusion protein lacking the amino terminal 13 amino acids, rSKΔ14 also showed a marked delay in time to activation of approximately 250 sec. (see FIG. 2). The lag phase refers to the time required for the reaction to the exponential phase of activity, e.g, full catalytic activity.

Plasmin cleavage products

Figure 3:
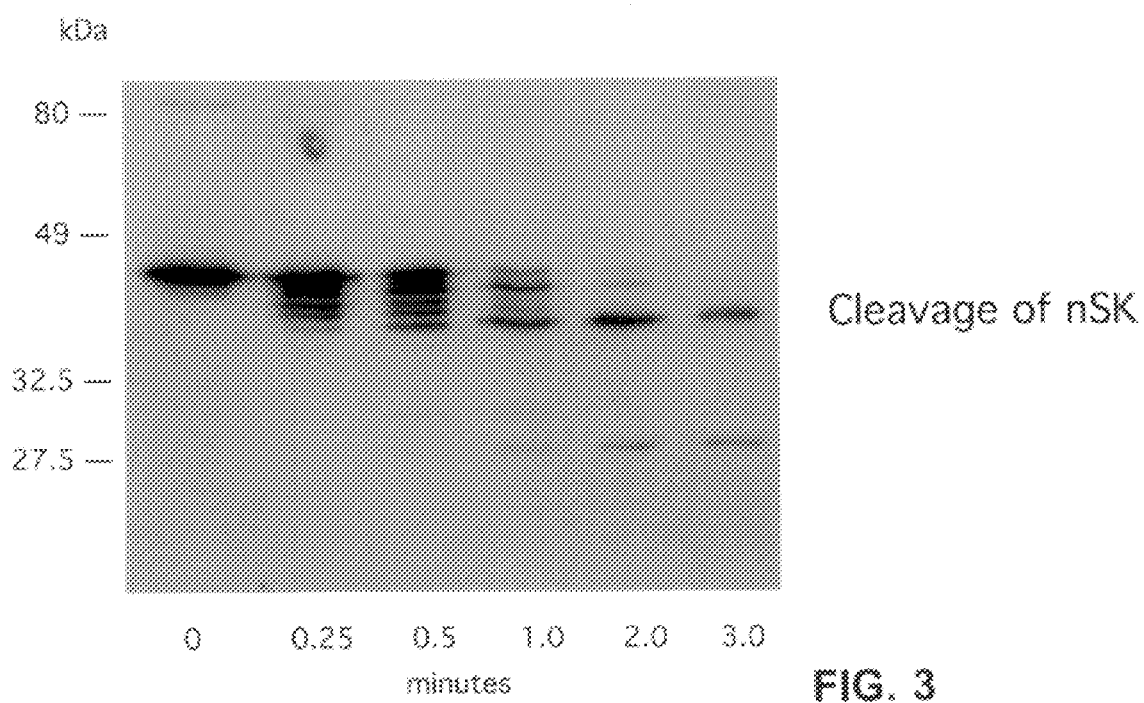
FIG. 3 is a photograph of a Western blot showing plasmin cleavage of nSK.
Figure 4:
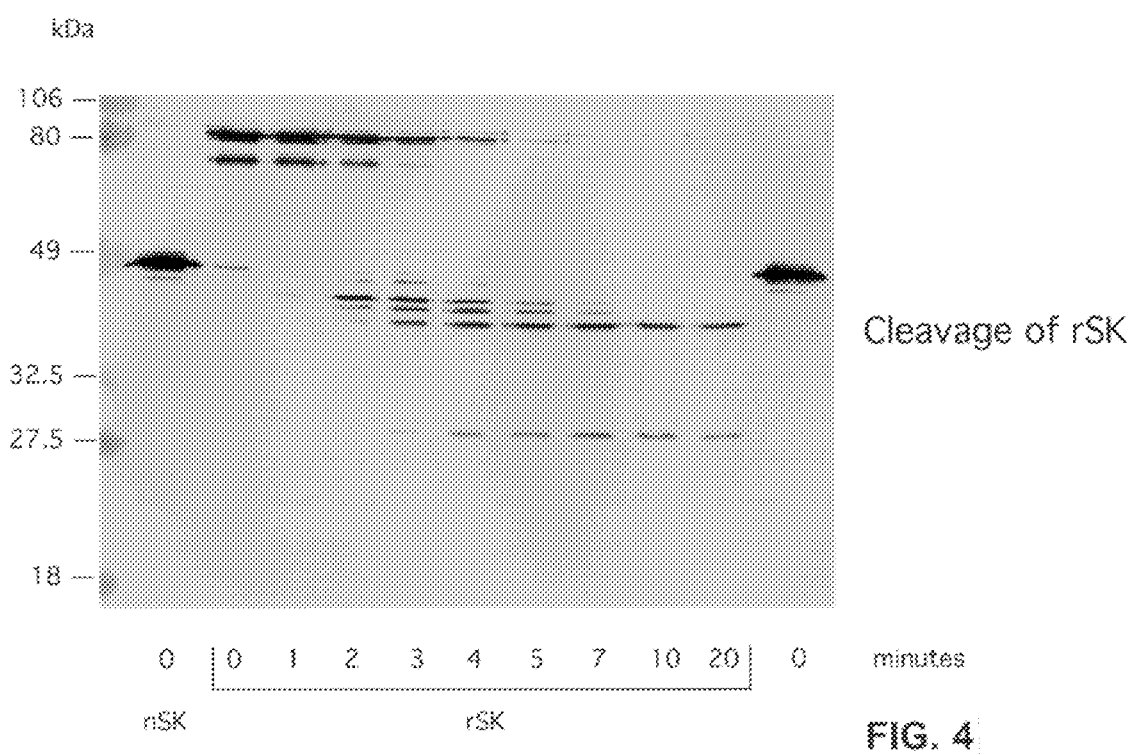
FIG. 4 is a photograph of a Western blot showing plasmin cleavage of rSK (0–20 min.).
Figure 5:
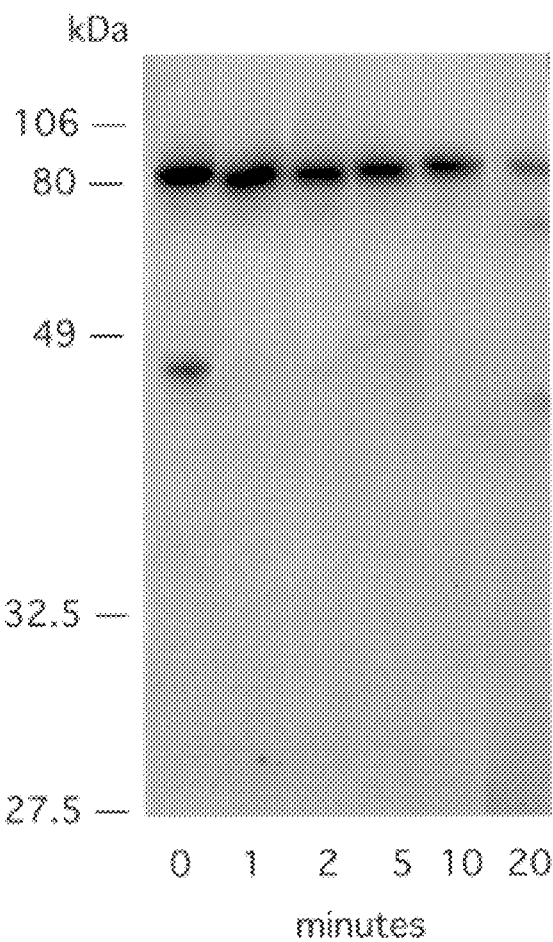
FIG. 5 is a photograph of a Western blot showing plasmin cleavage of rSKΔ14.

Since nSK is known to be cleaved by plasmin after formation of the SK-PAC, the rate of cleavage of rSK and rSKΔ14 was examined after various times of incubation with Glu-plasminogen. In these experiments, SK was mixed with an excess of plasminogen for various amounts of time and the resulting cleavage of SK was determined by immunoblotting with monoclonal anti-SK antibodies. nSK was found to be rapidly degraded by plasmin within 30 secs to four lower molecular weight species, predominantly a ~36 kDa fragment (see FIGS. 3 and 7). In contrast, the degradation of rSK was slower, yielding a fragment of 47 kDa (identical in size to nSK), first appearing at 1 min. A pattern of smaller SK fragments similar to that observed with nSK developed thereafter. After 5 min., a ~36 kDa SK fragment similar to that seen after nSK cleavage was found to be the major remnant from rSK (see FIGS. 4 and 7). Other lower molecular weight SK fragments, e.g., ~28 kDa, were also evident as cleavage products of nSK, and at later time points, of rSK. Plasmin cleavage products of rSKΔ14 are shown in FIG. 5.

Amino-terminal deletion of SK

The amino terminal 13 residues of SK are highly conserved among the SKs produced by different groups of streptococci. In addition, this region constitutes a major epitope for both murine and human antibodies against SK. Removal of the amino-terminal 13 amino acids from nSK resulted in a further increase in the lag phase of plasminogen activation by rSKΔ14, as compared to rSK. This lag phase was marked at 21° C., but shortened significantly when the temperature was raised to 37° C. Active site titration experiments indicate that removal of the amino terminus further delays the generation of the active site in the rSKΔ14.

Advantages of amino-terminally modified SK

At 37° C., and in vivo, nSK rapidly forms an active site with plasminogen. The kinetics of this activation has been regarded as suboptimal for therapy because plasmin is rapidly activated in one large burst in vivo. To overcome the explosive activation of plasminogen, an acylated SK-PAC (APSAC) made from SK and purified human plasminogen has been created in vitro (Ferres, 1987, Drugs 33 (Suppl. 3) 33). This approach permits APSAC to be given as a single bolus in vivo because continuous deacylation of the active site proceeds with a half-life of 40 mins (Staniforth et al., 1983, Eur. J. Clin. Pharmacol. 24:751). A limitation of this approach is that the rate of appearance of the active SK-PAC is determined by the rate of deacylation and can not be otherwise modulated.

In contrast, recombinant modification of the amino terminus of SK, either by expression as a fusion protein, or by deletion of the amino terminus, can predictably alter the rate of active site generation. For example, the extent to which the rate of degradation is reduced compared to nSK is directly proportional to the number of deleted amino-terminal amino acids (up to 13 amino acids). Other advantages of the SK-derived compounds of the invention include a short half-life: 2–4 min.; safety: the compounds of the invention are not made from human blood products; and cost-effectiveness: the compounds of the invention are recombinantly produced. The activity of the compounds is timed-released, therefore they can be administered in a single dose. The time required to achieve SK activity may also be modified depending on the number of amino-terminal amino acids removed from the nSK, i.e., length of time required is directly proportional to the number of amino acids deleted. In this manner, the timed-release activity of SK can be customized to suit the specific clinical application or patient to be treated. Thus, the compounds of the invention are improved clinical reagents because, using modified rSKs, an active SK-PAC can be generated at a rate consistent with best thrombolytic results.

EXAMPLE 2

Site-directed streptokinase mutants resist cleavage and degradation by plasmin

To examine the effects of cleavage on the activity of SK, site-directed mutations of R or L to A at putative plasmin or trypsin cleavage sites in the amino and carboxy terminus of SK were generated. The cleavage rate of these recombinant SKs were then examined. The catalytic function of rSKs with these specific mutations was also evaluated.

SK cloning and mutation by overlap extension

The SK gene was cloned from Group C *Streptococcus equisimilis* as described above. A series of mutations was performed in the amino terminus of SK to replace R or K residues with an A residue at putative plasmin cleavage sites. In addition, a single K to A mutation was constructed for K386 in the carboxy terminus of SK. PCR primers were used to produce site-directed mutations by the overlap extension method. For example, using nSK in the pMAL vector as a template, PCR was performed using a primer corresponding to the mal E sequence of the pMALc vector and the SK 10 AS primer. At the same time the SK 10 S primer was used in a PCR reaction with a SK 36 AS primer. The PCR products were purified on a low-melt agarose gel and used in an overlap PCR reaction. The overlapped product was then further amplified using the mal E primer and the SK 36 AS primer. In a similar fashion, the primers were used to construct mutations at the 45 and 51 position. The final overlap construct was between the 5' overlapped mutated SK segment containing the mutations at SK 10, 36, 45, and 51 and the segment from 51 to 127. This overlapped fragment was then ligated into the pMALc nSK, replacing the wild type sequence, between restriction sites for KpnI and AflII. The SK 59 mutation was separately constructed and used to replace the wild type sequence between AflII and MunI. The mutation at residue 386 was similarly constructed and ligated into SK using a HindIII site. The mutated pMALcSKs were sequenced to verify the desired mutations.

TABLE 5

Primers for Mutation by Overlap Extension

| Primer | Mutation | Primer Sequence | Restriction Site |
| --- | --- | --- | --- |
| SK 10 S | R−>A | 5'-GCTGCTAGACGCGCCATCTGTCAAC (SEQ ID NO: 5) | HhaI |
| SK 10 AS | | 5'-TGGCGCGTCTAGCAGCCACTCAG (SEQ ID NO: 6) | |
| SK 36 S | K−>A | 5'-CAAGACATTAGTCTGGCCTTTTTTGAAATCG (SEQ ID NO: 7) | HaeIII |
| SK 36 AS | | 5'-GGCCAGACTAATGTCTTGATTCG (SEQ ID NO: 8) | |
| SK 45 S | R −>A | 5'-CGATCTAACATCGGCGCCTGCTCATGG (SEQ ID NO: 9) | NarI |

TABLE 5-continued

Primers for Mutation by Overlap Extension

| Primer | Mutation | Primer Sequence | Restriction Site |
|---|---|---|---|
| SK 45 AS | | 5'-CGCCGATGTTAGATCGATTTC (SEQ ID NO: 10) | |
| SK 51 S | K->A | 5'-GCTCATGGAGGCGCCACAGAGGGC (SEQ ID NO: 11) | NarI |
| SK 51 AS | | 5'-GGCGCCTCCATGAGCAGGTC (SEQ ID NO: 12) | |
| SK 59 S | K->A | 5'-GCTTAAGTCCGGCCTCAAAACCATTTGC (SEQ ID NO: 13) | HaeIII |
| SK 59 AS | | 5'-TGAGGCCGGACTTAAGCCTTGCTC (SEQ ID NO: 14) | |
| SK 386S | K->A | 5'-GCCGATCGATATACCGAAGAAGAACGAG (SEQ ID NO: 15) 5'-TATCGATCGGCATCATAGGCTAAATGATAGC (SEQ ID NO: 16) | ClaI |

Plasmin-resistant SK site mutants

The following plasmin cleavage sites can be mutated: R10A, K36A, R45A, K51A, K59A, K61A, K147A, K333, R232A, K257A, K298A, K309A, R234A, R363A, K386A, K372A, R388A, R394A, and R401A. Single mutants K59A, K386A, were made, and the multiple mutant containing R10A, K36A, R45A, K51A, and K59A (rSKmut5) was studied further. Purification of rSK5mut is shown in FIG. 1. Multiple mutant rSK6mut is identical to rSK5mut with the addition of another mutation at a carboxy-terminal potential plasmin cleavage site. This mutant contains the following mutations: R10A, K36A, R45A, K51A, K59A and k386A.

Figure 6:
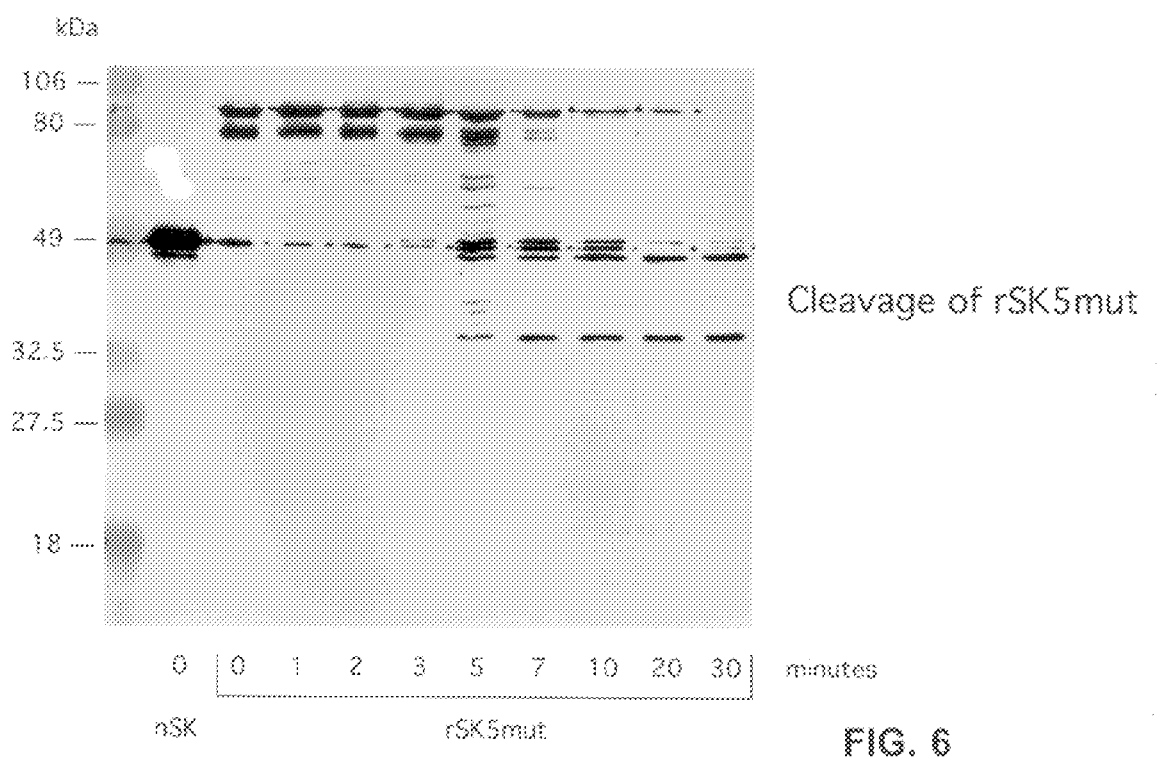
FIG. 6 is a photograph of a Western blot showing plasmin cleavage of rSK5mut.

The plasmin-resistant SK site mutants produce catalytically-active plasmin cleavage products which are larger than those generated from nSK (see FIGS. 6 and 7). The rate of degradation of rSK5mut is also slower than that of nSK (see FIGS. 6 and 7).

Kinetic studies were performed to examine the catalytic activity of the site mutants. Table 6 shows the results from kinetic studies for rSK5mut and Glu-plasminogen. These data show that mutation of plasmin cleavage sites significantly decreases the $K_m$ of SK amidolytic activity leading to greater catalytic efficiency, and thus, greater therapeutic efficacy.

TABLE 6

Kinetic Parameters for recombinant SKS and Glu-Plasminogen

| | $K_m$ ($\mu M$) | $K_{cat}$ ($S^{-1}$) | $k_{cat}/K_m$ ($\mu M^{-1} S^{-1}$) |
|---|---|---|---|
| nSK | 248 | 56 | 0.226 |
| rSK | 152 | 42 | 0.276 |
| rSKΔ14 | 533 | 51 | 0.096 |
| rSK5mut | 77 | 52 | 0.675 |

TABLE 7 rSK5mut

MKTEEGKLVI WI NGDKGYNGLAE VGKKFEKDTGI KVTVEHPDKLEEKFP QVAATGDGPDI
I F WAHDRFGGYAQSGLLAEI TPDKAFQDKLYPFTWDAVRYNGKLI AYPI AVEALSLI YNK
DLLPNPPKTWEEI PALDKELAAKGKS AL MFNLQEP YFTWPLI AADGGYAFKYENGKYDI K
DVGVDNAGAKAGLTFLVDLI KNKHMNADTDYSI AEAAFNKGETAMTI NGPWAWSNI DTSK
VNYGVTVLPTFKGQPSKPFVGVLSAGI NAASPNKELAKEFLENYLLTDEGLEAVNKDKPL
GAVALKSYEEELAKDPRI AATMENAQKGEI MPNI PQMSAFWYAVRTAVI NAASGRQTVDE
ALKDAQTNSSSVPGRGSI EGRI AGPEWLLDAPSVNNSQLVVSVAGTVEGTNQDI SLAFFE
I DLTSAPAHGGATEQGLSPASKPFATDSGAMSHKLEKADLLKAI QEQLI AVVHSNDDYFE
VI DFASDATI TDRNGKVYFAPKDGSVTLPTQPVQEFLLSGHVRVRYKEKPI QNQAKSVDV
EYTVQFTPLNPDDDFRPGLKDTKLLKTLAI GDTI TSQELLAQAQSI LNKNHPGYTI YERD
SSI VTHDNDI FRTI LPMDQEFTYRVKNREQAYRI NKKSGLNEEI NNTDLI SEKYYVLKKG
EKPYDPFDRSHLKLFTI KYVDVDTNELLKSEQLLTASERNLDFRDLYDPRDKAKLLYNNL
DAFGI MDYTLTGKVEDNHDDTNRI I TVYMGKRPEGENASYHLAYDKDRYTEEEREVYSYL
RYTGTPI PDNPNDKNNSQLVVSVAGTVEGTNQDI SLKFFEI DLTSRPAHGGKTEQGLSPK
SKPFATDSGAMSHKLEKADLLKAI QEQLI ANVHSNDDYFEVI DFASDATI TDRNGKVYF
ADKDGSVTLPTQPVQEFLLSGHVRVRYKEKPI QNQAKSVDVEYTVQFTPLNPDDDFRPGL
KDTKLLKTLAI GDTI TSQELLAQAQSI LNKNHPGYTI YERDSSI VTHDNDI FRTI LPMDQ
EFTYRVKNREQAYRI NKKSGLNEEI NNTDLI SEKYYVLKKGEKPYDPFDRSHLKLFTI KY
VDVDTNELLKSEQLLTASERNLDFRDLYDPRDKAKLLYNNLDAFGI MDYTLTGKVEDNHD
DTNRI I TVYMGKRPEGENASYHLAYDKDRYTEEEREVYS YLRYTGTPI PDNPNDK (SEQ
ID NO: 17)

TABLE 8 rSK6mut

MKTEEGKLVI WI NGDKGYNGLAEVGKKFEKDTGI KVTVEHPDKLEEKFPQVAATGDGPDI
I FWAHDRFGGYAQS GLLAEI TPDKAFQDKLYPFTWDAVRYNGKLI AYPI AVEALSLI YNK
DLLPNPPKTWEEI PALDKELKAKGKS ALMFNLQEPYFTWPLI AADGGYAFKYENGKYDI K
DVGVDNAGAKAGLTFLVDLI KNKHMNADTDYSI AEAAFNKGETAMTI NGPWAWSNI DTSK
VNYGVTVLPTFKGQPS KPFVGVLS AGI NAAS PNKELAKEFLENYLLTDEGLEAVNKDKPL
GAVALKS YEEELAKDPRI AATMENAQKGEI MPNI PQMS AFWYAVRTAVI NAAS GRQTVDE
ALKDAQTNSS S VPGRGSI EGRI AGPEWLLDAPSVNNSQLVVS VAGTVEGTNQDI SLAFFE
I DLTSAPAHGGATEQGLS PAS KPFATDS GAMS HKLEKADLLKAI QEQLI ANVHSNDDYFE
VI DFASDATI TDRNGKVYFADKDGS VTLPTQPVQEFLLS GHVRVRYKEKPI QNQAKS VDV
EYTVQFTPLNPDDDFRPGLKDTKLLKTLAI GDTI TSQELLAQAQSI LNKNHPGYTI YERD
SSI VTHDNDI FRTI LPMDQEFTYRVKNREQAYRI NKKS GLNEEI NNTDLI SEKYYVLKKG
EKPYDPFDRS HLKLFTI KYVDVDTNELLKS EQLLTASERNLDFRDLYDPRDKAKLLYNNL
DAFGI MDYTLTGKVEDNHDDTNRI I TVYMGKRPEGENAS YHLAYDADRYTEEEREVYSYL
RYTGTPI PDNPNDKNNSQLVVS VAGTVEGTNQDI SLKFFEI DLTS RPAHGGKTEQGLS PK
SKPFATDS GAMS HKLEKADLLKAI QEQLI ANVHSNDDYFEVI DFASDATI TDRNGKVYF
ADKDGS VTLPTQPVQEFLLS GHVRVRYKEKPI QNQAKS VDVEYTVQFTPLNPDDDFRPGL
KDTKLLKTLAI GDTI TSQELLAQAQSI LNKNHPGYTI YERDSSI VTHDNDI FRTI LPMDQ
EFTYRVKNREQAYRI NKKS GLNEEI NNTDLI SEKYYVLKKGEKPYDPFDRS HLKLFTI KY
VDVDTNELLKS EQLLTASERNLDFRDLYDPRDKAKLLYNNLDAFGI MDYTLTGKVEDNHD
DTNRI I TVYMGKRPEGENAS YHLAYDKDRYTEEEREVYS YLRYTGTPI PDNPNDK (SEQ ID NO: 18)

TABLE 9

DNA sequence of SK from *S. equisimilus* H46A

| | | | | |
|---|---|---|---|---|
| 1 | ctgcagctac | ctgataccag | gcatttccaa | caaacatggt | taaggccaaa |
| 51 | ccaaaatcac | tttctagcgt | tggcaagaga | ccttcaagcg | agcgcaagac |
| 101 | ctttattgaa | gttgcttgtc | gacataaaaa | tgctgtttgg | gttgtgctga |
| 151 | taggcaaaat | gacctcaagc | cctgcaatca | tctgctggag | caactcaact |
| 201 | aagtcagctg | gtaaaacctg | ctgatgattg | aggtaaataa | actgagaagt |
| 251 | ctcaaacagc | tgaggggggat | tgccctgatg | atcaagcaaa | taccgctgcc |
| 301 | aaggtgaccc | tagcggctgc | aagacctcat | attgacccaa | ccccacctca |
| 351 | agtaataagc | gctcttttc | ggataaacat | gatttgggaa | aatgcacata |
| 401 | ttggtcccct | tctttgacac | tcacccactc | tttatctcct | aacggatgag |
| 451 | ggcctacttg | catctctgga | aaatagtctt | ttagctccat | agccattcct |
| 501 | ttcatgacgg | tctttaaacc | attataacac | atgactcttt | atcacacagt |
| 551 | tcagtttgtt | gtcagcacga | ttttgtattt | tctgccttt | taatcattaa |
| 601 | aactaaataa | gggttattca | tttttaqcaa | gaacattcaa | ttaaatagct |
| 651 | atttatcgga | atattaattt | atgtttatgc | taaaaaaggt | attatttacc |
| 701 | tttttttcatt | gtcattaaaa | tatctttta | aaaaaatcaa | taggttttta |
| 751 | tttgtgtctt | taaaaccatt | atgttattct | aataatgggg | attgaaactt |
| 801 | aacttttagg | aggtttctat | gaaaaattac | ttatcttttg | ggatgtttgc |
| 851 | actgctgttt | gcactaacat | ttggaacagt | caattctgtc | caagctattg |
| 901 | ctggacctga | gtggctgcta | gaccgtccat | ctgtcaacaa | cagccaatta |
| 951 | gttgttagcg | ttgctggtac | tgttgagggg | acgaatcaag | acattagtct |
| 1001 | taaattttt | gaaatcgatc | taacatcacg | acctgctcat | aggaaaga |
| 1051 | cagagcaagg | cttaagtcca | aaatcaaaac | catttgctac | tgatagtggc |
| 1101 | gcgatgtcac | ataaacttga | gaaagctgac | ttactaaagg | ctattcaaga |
| 1151 | acaattgatc | gctaacgtcc | acagtaacga | cgactacttt | gaggtcattg |
| 1201 | attttgcaag | cgatgcaacc | attactgatc | gaaacggcaa | ggtctacttt |
| 1251 | gctgacaaag | atggttcggt | aaccttgccg | acccaacctg | tccaagaatt |
| 1301 | tttgctaagc | ggacatgtgc | gcgttagacc | atataagaa | aaaccaatac |
| 1351 | aaaaccaagc | gaaatctgtt | gatgtggaat | atactgtaca | gtttactccc |
| 1401 | ttaaaccctg | atgacgattt | cagaccaggt | ctcaaagata | ctaagctatt |
| 1451 | gaaaacacta | gctatcggtg | acaccatcac | atctcaagaa | ttactagctc |
| 1501 | aagcacaaag | cattttaaac | aaaaaccacc | caggctatac | gatttatgaa |
| 1551 | cgtgactcct | caatcgtcac | tcatgacaat | gacattttcc | gtacgatttt |
| 1601 | accaatggat | caagagttta | cttaccgtgt | taaaaatcgg | gaacaagctt |
| 1651 | ataggatcaa | taaaaaatct | ggtctgaatg | aagaaataaa | caacactgac |
| 1701 | ctgatctctg | agaaatatta | cgtcctaaaa | aaaggggaaa | agccgtatga |
| 1751 | tcccttttgat | cgcagtcact | tgaaactgtt | caccatcaaa | tacgttgatg |
| 1801 | tcgataccaa | cgaattgcta | aaaagtgagc | agctcttaac | agctagcgaa |
| 1851 | cgtaacttag | acttcagaga | tttatacgat | cctcgtgata | aggctaaact |
| 1901 | actctacaac | aatctcgatg | cttttggtat | tatggactat | accttaactg |
| 1951 | gaaaagtaga | ggataatcac | gatgacacca | accgtatcat | aaccgtttat |
| 2001 | atgggcaagc | gacccgaagg | agagaatgct | agctatcatt | tagcctatga |
| 2051 | taaagatcgt | tataccgaag | aagaacgaga | agtttacagc | tacctgcgtt |
| 2101 | atacagggac | acctatacct | gataaccctaa | acgacaaata | accacggtct |
| 2151 | tctaaaacga | tgagattaac | tgacaaaaaa | agcaagcaac | atgctatcaa |
| 2201 | cagttgcttg | cttttttcta | acctcttagt | tgtagagact | agtgacattt |
| 2251 | cgtgtctaaa | ataatcgtaa | ctggtccatc | attgatgaga | ctaacctgca |
| 2301 | tatctgcccc | aaaaacgcca | cgctcaactg | gcacaaaatc | tgccaattgt |
| 2351 | tcattaaagc | gatcataaaa | ctggctagcc | atatcagctt | tgcagctcct |

TABLE 9-continued

DNA secruence of SK from *S. equisimilus* H46A

| 2401 | gtaaaggctg | ggcgatttcc | cttttggtg | tcagcataaa | gggtaaattg |
|------|------------|------------|-----------|------------|------------|
| 2451 | cgacacagat | aagatactac | ccttgatgtc | ttggatagac | tgattcatct |
| 2501 | tgccatcagc | atctgaaaaa | atgcgcatgt | tgactatttt | tgcacagcgt |
| 2551 | aagccaaatc | ttctgcag | | | |

(SEQ ID NO: 19)

SK coding sequence spans nucleotides 819–2138; coding sequence of mature peptide spans nucleotides 891–2138.

TABLE 9

DNA seguence of MBP*

| | | | | |
|---|---|---|---|---|
| atgaaaactg | aagaaggtaa | actggtaatc | tggattaacg | gcgataaagg |
| ctataacggt | ctcgctgaag | tcggtaagaa | attcgagaaa | gataccggaa |
| ttaaagtcac | cgttgagcat | ccggataaac | tggaagagaa | attcccacag |
| gttgcggcaa | ctggcgatgg | ccctgacatt | atcttctggg | cacacgaccg |
| ctttggtggc | tacgctcaat | ctggcctgtt | ggctgaaatc | accccggaca |
| aagcgttcca | ggacaagctg | tatccgttta | cctgggatgc | cgtacgttac |
| aacggcaagc | tgattgctta | cccgatcgct | gttgaagcgt | tatcgctgat |
| ttataacaaa | gatctgctgc | cgaacccgcc | aaaaacctgg | gaagagatcc |
| cggcgctgga | taaagaactg | aaagcgaaag | gtaagagcgc | gctgatgttc |
| aacctgcaag | aaccgtactt | cacctggccg | ctgattgctg | ctgacggggg |
| ttatgcgttc | aagtatgaaa | acggcaagta | cgacattaaa | gacgtgggcg |
| tggataacgc | tggcgcgaaa | gcgggtctga | ccttcctggt | tgacctgatt |
| aaaaacaaac | acatgaatgc | agacaccgat | tactccatcg | cagaagctgc |
| ctttaataaa | ggcgaaacag | cgatgaccat | caacggcccg | tgggcatggt |
| ccaacatcga | caccagcaaa | gtgaattatg | gtgtaacggt | actgccgacc |
| ttcaagggtc | aaccatccaa | accgttcgtt | ggcgtgctga | gcgcaggtat |
| taacgccgcc | agtccgaaca | aagagctggc | gaaagagttc | ctcgaaaact |
| atctgctgac | tgatgaaggt | ctggaagcgg | ttaataaaga | caaaccgctg |
| ggtgccgtag | cgctgaagtc | ttacgaggaa | gagttggcga | aagatccacg |
| tattgccgcc | accatggaaa | acgcccagaa | aggtgaaatc | atgccgaaca |
| tcccgcagat | gtccgctttc | tggtatgccg | tgcgtactgc | ggtgatcaac |
| gccgcagcg | gtcgtcagac | tgtcgatgaa | gccctgaaag | acgcgcagac |
| taattcgagc | tcggtacccg | gccggggatc | catcgagggt | agg |

(SEQ ID NO: 20)

*sequence represents cDNA sequence of MBP up to the restriction site in the polylinker where cDNA encoding SK was inserted.

---

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1194 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:1:

```
Met  Lys  Thr  Glu  Glu  Gly  Lys  Leu  Val  Ile  Trp  Ile  Asn  Gly  Asp  Lys
 1                    5                            10                           15

Gly  Tyr  Asn  Gly  Leu  Ala  Glu  Val  Gly  Lys  Lys  Phe  Glu  Lys  Asp  Thr
              20                           25                           30

Gly  Ile  Lys  Val  Thr  Val  Glu  His  Pro  Asp  Lys  Leu  Glu  Glu  Lys  Phe
         35                            40                           45

Pro  Gln  Val  Ala  Ala  Thr  Gly  Asp  Gly  Pro  Asp  Ile  Ile  Phe  Trp  Ala
```

```
                    50                          55                           60
His  Asp  Arg  Phe  Gly  Gly  Tyr  Ala  Gln  Ser  Gly  Leu  Leu  Ala  Glu  Ile
 65                      70                       75                            80

Thr  Pro  Asp  Lys  Ala  Phe  Gln  Asp  Lys  Leu  Tyr  Pro  Phe  Thr  Trp  Asp
                         85                       90                            95

Ala  Val  Arg  Tyr  Asn  Gly  Lys  Leu  Ile  Ala  Tyr  Pro  Ile  Ala  Val  Glu
                        100                      105                           110

Ala  Leu  Ser  Leu  Ile  Tyr  Asn  Lys  Asp  Leu  Leu  Pro  Asn  Pro  Pro  Lys
               115                      120                      125

Thr  Trp  Glu  Glu  Ile  Pro  Ala  Leu  Asp  Lys  Glu  Leu  Lys  Ala  Lys  Gly
          130                      135                      140

Lys  Ser  Ala  Leu  Met  Phe  Asn  Leu  Gln  Glu  Pro  Tyr  Phe  Thr  Trp  Pro
145                     150                      155                           160

Leu  Ile  Ala  Ala  Asp  Gly  Gly  Tyr  Ala  Phe  Lys  Tyr  Glu  Asn  Gly  Lys
                    165                      170                      175

Tyr  Asp  Ile  Lys  Asp  Val  Gly  Val  Asp  Asn  Ala  Gly  Ala  Lys  Ala  Gly
                    180                      185                      190

Leu  Thr  Phe  Leu  Val  Asp  Leu  Ile  Lys  Asn  Lys  His  Met  Asn  Ala  Asp
          195                      200                      205

Thr  Asp  Tyr  Ser  Ile  Ala  Glu  Ala  Ala  Phe  Asn  Lys  Gly  Glu  Thr  Ala
     210                      215                      220

Met  Thr  Ile  Asn  Gly  Pro  Trp  Ala  Trp  Ser  Asn  Ile  Asp  Thr  Ser  Lys
225                     230                      235                           240

Val  Asn  Tyr  Gly  Val  Thr  Val  Leu  Pro  Thr  Phe  Lys  Gly  Gln  Pro  Ser
                    245                      250                      255

Lys  Pro  Phe  Val  Gly  Val  Leu  Ser  Ala  Gly  Ile  Asn  Ala  Ala  Ser  Pro
                    260                      265                      270

Asn  Lys  Glu  Leu  Ala  Lys  Glu  Phe  Leu  Glu  Asn  Tyr  Leu  Leu  Thr  Asp
          275                      280                      285

Glu  Gly  Leu  Glu  Ala  Val  Asn  Lys  Asp  Lys  Pro  Leu  Gly  Ala  Val  Ala
     290                      295                      300

Leu  Lys  Ser  Tyr  Glu  Glu  Glu  Leu  Ala  Lys  Asp  Pro  Arg  Ile  Ala  Ala
305                     310                      315                           320

Thr  Met  Glu  Asn  Ala  Gln  Lys  Gly  Glu  Ile  Met  Pro  Asn  Ile  Pro  Gln
                    325                      330                      335

Met  Ser  Ala  Phe  Trp  Tyr  Ala  Val  Arg  Thr  Ala  Val  Ile  Asn  Ala  Ala
               340                      345                      350

Ser  Gly  Arg  Gln  Thr  Val  Asp  Glu  Ala  Leu  Lys  Asp  Ala  Gln  Thr  Asn
          355                      360                      365

Ser  Ser  Ser  Val  Pro  Gly  Arg  Gly  Ser  Ile  Glu  Gly  Arg  Ile  Ala  Gly
     370                      375                      380

Pro  Glu  Trp  Leu  Leu  Asp  Arg  Pro  Ser  Val  Asn  Asn  Ser  Gln  Leu  Val
385                     390                      395                           400

Val  Ser  Val  Ala  Gly  Thr  Val  Glu  Gly  Thr  Asn  Gln  Asp  Ile  Ser  Leu
                    405                      410                      415

Lys  Phe  Phe  Glu  Ile  Asp  Leu  Thr  Ser  Arg  Pro  Ala  His  Gly  Gly  Lys
                    420                      425                      430

Thr  Glu  Gln  Gly  Leu  Ser  Pro  Lys  Ser  Lys  Pro  Phe  Ala  Thr  Asp  Ser
          435                      440                      445

Gly  Ala  Met  Ser  His  Lys  Leu  Glu  Lys  Ala  Asp  Leu  Leu  Lys  Ala  Ile
     450                      455                      460

Gln  Glu  Gln  Leu  Ile  Ala  Asn  Val  His  Ser  Asn  Asp  Asp  Tyr  Phe  Glu
465                     470                      475                           480
```

```
Val  Ile  Asp  Phe  Ala  Ser  Asp  Ala  Thr  Ile  Thr  Asp  Arg  Asn  Gly  Lys
                    485                 490                      495

Val  Tyr  Phe  Ala  Asp  Lys  Asp  Gly  Ser  Val  Thr  Leu  Pro  Thr  Gln  Pro
                    500                 505                      510

Val  Gln  Glu  Phe  Leu  Leu  Ser  Gly  His  Val  Arg  Val  Arg  Tyr  Lys  Glu
               515                 520                      525

Lys  Pro  Ile  Gln  Asn  Gln  Ala  Lys  Ser  Val  Asp  Val  Glu  Tyr  Thr  Val
     530                      535                      540

Gln  Phe  Thr  Pro  Leu  Asn  Pro  Asp  Asp  Phe  Arg  Pro  Gly  Leu  Lys
545                      550                 555                           560

Asp  Thr  Lys  Leu  Leu  Lys  Thr  Leu  Ala  Ile  Gly  Asp  Thr  Ile  Thr  Ser
                    565                 570                      575

Gln  Glu  Leu  Leu  Ala  Gln  Ala  Gln  Ser  Ile  Leu  Asn  Lys  Asn  His  Pro
               580                 585                      590

Gly  Tyr  Thr  Ile  Tyr  Glu  Arg  Asp  Ser  Ser  Ile  Val  Thr  His  Asp  Asn
               595                 600                      605

Asp  Ile  Phe  Arg  Thr  Ile  Leu  Pro  Met  Asp  Gln  Glu  Phe  Thr  Tyr  Arg
     610                      615                 620

Val  Lys  Asn  Arg  Glu  Gln  Ala  Tyr  Arg  Ile  Asn  Lys  Lys  Ser  Gly  Leu
625                      630                 635                           640

Asn  Glu  Glu  Ile  Asn  Asn  Thr  Asp  Leu  Ile  Ser  Glu  Lys  Tyr  Tyr  Val
                    645                 650                      655

Leu  Lys  Lys  Gly  Glu  Lys  Pro  Tyr  Asp  Pro  Phe  Asp  Arg  Ser  His  Leu
               660                 665                      670

Lys  Leu  Phe  Thr  Ile  Lys  Tyr  Val  Asp  Val  Asp  Thr  Asn  Glu  Leu  Leu
               675                 680                      685

Lys  Ser  Glu  Gln  Leu  Leu  Thr  Ala  Ser  Glu  Arg  Asn  Leu  Asp  Phe  Arg
     690                      695                      700

Asp  Leu  Tyr  Asp  Pro  Arg  Asp  Lys  Ala  Lys  Leu  Leu  Tyr  Asn  Asn  Leu
705                      710                 715                           720

Asp  Ala  Phe  Gly  Ile  Met  Asp  Tyr  Thr  Leu  Thr  Gly  Lys  Val  Glu  Asp
                    725                 730                      735

Asn  His  Asp  Asp  Thr  Asn  Arg  Ile  Ile  Thr  Val  Tyr  Met  Gly  Lys  Arg
               740                 745                      750

Pro  Glu  Gly  Glu  Asn  Ala  Ser  Tyr  His  Leu  Ala  Tyr  Asp  Lys  Asp  Arg
     755                      760                      765

Tyr  Thr  Glu  Glu  Glu  Arg  Glu  Val  Tyr  Ser  Tyr  Leu  Arg  Tyr  Thr  Gly
     770                      775                      780

Thr  Pro  Ile  Pro  Asp  Asn  Pro  Asn  Asp  Lys  Asn  Asn  Ser  Gln  Leu  Val
785                      790                 795                           800

Val  Ser  Val  Ala  Gly  Thr  Val  Glu  Gly  Thr  Asn  Gln  Asp  Ile  Ser  Leu
                    805                 810                      815

Lys  Phe  Phe  Glu  Ile  Asp  Leu  Thr  Ser  Arg  Pro  Ala  His  Gly  Gly  Lys
               820                 825                      830

Thr  Glu  Gln  Gly  Leu  Ser  Pro  Lys  Ser  Lys  Pro  Phe  Ala  Thr  Asp  Ser
          835                      840                 845

Gly  Ala  Met  Ser  His  Lys  Leu  Glu  Lys  Ala  Asp  Leu  Leu  Lys  Ala  Ile
          850                 855                      860

Gln  Glu  Gln  Leu  Ile  Ala  Asn  Val  His  Ser  Asn  Asp  Asp  Tyr  Phe  Glu
865                      870                      875                      880

Val  Ile  Asp  Phe  Ala  Ser  Asp  Ala  Thr  Ile  Thr  Asp  Arg  Asn  Gly  Lys
                    885                 890                      895

Val  Tyr  Phe  Ala  Asp  Lys  Asp  Gly  Ser  Val  Thr  Leu  Pro  Thr  Gln  Pro
                    900                 905                      910
```

```
Val  Gln  Glu  Phe  Leu  Leu  Ser  Gly  His  Val  Arg  Val  Arg  Tyr  Lys  Glu
          915                      920                 925

Lys  Pro  Ile  Gln  Asn  Gln  Ala  Lys  Ser  Val  Asp  Val  Glu  Tyr  Thr  Val
     930                      935                 940

Gln  Phe  Thr  Pro  Leu  Asn  Pro  Asp  Asp  Asp  Phe  Arg  Pro  Gly  Leu  Lys
945                      950                      955                      960

Asp  Thr  Lys  Leu  Leu  Lys  Thr  Leu  Ala  Ile  Gly  Asp  Thr  Ile  Thr  Ser
                    965                      970                      975

Gln  Glu  Leu  Leu  Ala  Gln  Ala  Gln  Ser  Ile  Leu  Asn  Lys  Asn  His  Pro
               980                      985                      990

Gly  Tyr  Thr  Ile  Tyr  Glu  Arg  Asp  Ser  Ser  Ile  Val  Thr  His  Asp  Asn
          995                     1000                    1005

Asp  Ile  Phe  Arg  Thr  Ile  Leu  Pro  Met  Asp  Gln  Glu  Phe  Thr  Tyr  Arg
         1010                    1015                    1020

Val  Lys  Asn  Arg  Glu  Gln  Ala  Tyr  Arg  Ile  Asn  Lys  Lys  Ser  Gly  Leu
1025                    1030                    1035                         1040

Asn  Glu  Glu  Ile  Asn  Asn  Thr  Asp  Leu  Ile  Ser  Glu  Lys  Tyr  Tyr  Val
                   1045                    1050                    1055

Leu  Lys  Lys  Gly  Glu  Lys  Pro  Tyr  Asp  Pro  Phe  Asp  Arg  Ser  His  Leu
               1060                    1065                    1070

Lys  Leu  Phe  Thr  Ile  Lys  Tyr  Val  Asp  Val  Asp  Thr  Asn  Glu  Leu  Leu
              1075                    1080                    1085

Lys  Ser  Glu  Gln  Leu  Leu  Thr  Ala  Ser  Glu  Arg  Asn  Leu  Asp  Phe  Arg
              1090                    1095                    1100

Asp  Leu  Tyr  Asp  Pro  Arg  Asp  Lys  Ala  Lys  Leu  Leu  Tyr  Asn  Asn  Leu
1105                    1110                    1115                         1120

Asp  Ala  Phe  Gly  Ile  Met  Asp  Tyr  Thr  Leu  Thr  Gly  Lys  Val  Glu  Asp
                   1125                    1130                         1135

Asn  His  Asp  Asp  Thr  Asn  Arg  Ile  Ile  Thr  Val  Tyr  Met  Gly  Lys  Arg
              1140                    1145                    1150

Pro  Glu  Gly  Glu  Asn  Ala  Ser  Tyr  His  Leu  Ala  Tyr  Asp  Lys  Asp  Arg
              1155                    1160                    1165

Tyr  Thr  Glu  Glu  Glu  Arg  Glu  Val  Tyr  Ser  Tyr  Leu  Arg  Tyr  Thr  Gly
     1170                    1175                    1180

Thr  Pro  Ile  Pro  Asp  Asn  Pro  Asn  Asp  Lys
1185                    1190
```

( 2 ) INFORMATION FOR SEQ ID NO:2:

( i ) SEQUENCE CHARACTERISTICS:
        ( A ) LENGTH: 1181 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:2:

```
Met  Lys  Thr  Glu  Glu  Gly  Lys  Leu  Val  Ile  Trp  Ile  Asn  Gly  Asp  Lys
  1                 5                       10                          15

Gly  Tyr  Asn  Gly  Leu  Ala  Glu  Val  Gly  Lys  Lys  Phe  Glu  Lys  Asp  Thr
               20                      25                          30

Gly  Ile  Lys  Val  Thr  Val  Glu  His  Pro  Asp  Lys  Leu  Glu  Glu  Lys  Phe
          35                      40                          45

Pro  Gln  Val  Ala  Ala  Thr  Gly  Asp  Gly  Pro  Asp  Ile  Ile  Phe  Trp  Ala
     50                      55                          60
```

| His | Asp | Arg | Phe | Gly | Gly | Tyr | Ala | Gln | Ser | Gly | Leu | Leu | Ala | Glu | Ile |
| --- | --- | --- | --- | --- | --- | --- | --- | --- | --- | --- | --- | --- | --- | --- | --- |
| 65 | | | | | 70 | | | | 75 | | | | | | 80 |
| Thr | Pro | Asp | Lys | Ala | Phe | Gln | Asp | Lys | Leu | Tyr | Pro | Phe | Thr | Trp | Asp |
| | | | | 85 | | | | | 90 | | | | | 95 | |
| Ala | Val | Arg | Tyr | Asn | Gly | Lys | Leu | Ile | Ala | Tyr | Pro | Ile | Ala | Val | Glu |
| | | | | 100 | | | | | 105 | | | | | 110 | |
| Ala | Leu | Ser | Leu | Ile | Tyr | Asn | Lys | Asp | Leu | Leu | Pro | Asn | Pro | Pro | Lys |
| | | | 115 | | | | | 120 | | | | 125 | | | |
| Thr | Trp | Glu | Glu | Ile | Pro | Ala | Leu | Asp | Lys | Glu | Leu | Lys | Ala | Lys | Gly |
| | 130 | | | | | 135 | | | | | 140 | | | | |
| Lys | Ser | Ala | Leu | Met | Phe | Asn | Leu | Gln | Glu | Pro | Tyr | Phe | Thr | Trp | Pro |
| 145 | | | | | 150 | | | | | 155 | | | | | 160 |
| Leu | Ile | Ala | Ala | Asp | Gly | Gly | Tyr | Ala | Phe | Lys | Tyr | Glu | Asn | Gly | Lys |
| | | | | 165 | | | | | 170 | | | | | 175 | |
| Tyr | Asp | Ile | Lys | Asp | Val | Gly | Val | Asp | Asn | Ala | Gly | Ala | Lys | Ala | Gly |
| | | | 180 | | | | | 185 | | | | 190 | | | |
| Leu | Thr | Phe | Leu | Val | Asp | Leu | Ile | Lys | Asn | Lys | His | Met | Asn | Ala | Asp |
| | | 195 | | | | | 200 | | | | | 205 | | | |
| Thr | Asp | Tyr | Ser | Ile | Ala | Glu | Ala | Ala | Phe | Asn | Lys | Gly | Glu | Thr | Ala |
| | 210 | | | | | 215 | | | | | 220 | | | | |
| Met | Thr | Ile | Asn | Gly | Pro | Trp | Ala | Trp | Ser | Asn | Ile | Asp | Thr | Ser | Lys |
| 225 | | | | | 230 | | | | | 235 | | | | | 240 |
| Val | Asn | Tyr | Gly | Val | Thr | Val | Leu | Pro | Thr | Phe | Lys | Gly | Gln | Pro | Ser |
| | | | | 245 | | | | | 250 | | | | | 255 | |
| Lys | Pro | Phe | Val | Gly | Val | Leu | Ser | Ala | Gly | Ile | Asn | Ala | Ala | Ser | Pro |
| | | | | 260 | | | | | 265 | | | | | 270 | |
| Asn | Lys | Glu | Leu | Ala | Lys | Glu | Phe | Leu | Glu | Asn | Tyr | Leu | Leu | Thr | Asp |
| | | | 275 | | | | | 280 | | | | | 285 | | |
| Glu | Gly | Leu | Glu | Ala | Val | Asn | Lys | Asp | Lys | Pro | Leu | Gly | Ala | Val | Ala |
| | | 290 | | | | | 295 | | | | | 300 | | | |
| Leu | Lys | Ser | Tyr | Glu | Glu | Glu | Leu | Ala | Lys | Asp | Pro | Arg | Ile | Ala | Ala |
| 305 | | | | | 310 | | | | | 315 | | | | | 320 |
| Thr | Met | Glu | Asn | Ala | Gln | Lys | Gly | Glu | Ile | Met | Pro | Asn | Ile | Pro | Gln |
| | | | | 325 | | | | | 330 | | | | | 335 | |
| Met | Ser | Ala | Phe | Trp | Tyr | Ala | Val | Arg | Thr | Ala | Val | Ile | Asn | Ala | Ala |
| | | | | 340 | | | | | 345 | | | | | 350 | |
| Ser | Gly | Arg | Gln | Thr | Val | Asp | Glu | Ala | Leu | Lys | Asp | Ala | Gln | Thr | Asn |
| | | | 355 | | | | | 360 | | | | | 365 | | |
| Ser | Ser | Ser | Val | Pro | Gly | Arg | Gly | Ser | Ile | Glu | Gly | Arg | Asn | Asn | Ser |
| | | 370 | | | | | 375 | | | | | 380 | | | |
| Gln | Leu | Val | Val | Ser | Val | Ala | Gly | Thr | Val | Glu | Gly | Thr | Asn | Gln | Asp |
| 385 | | | | | 390 | | | | | 395 | | | | | 400 |
| Ile | Ser | Leu | Lys | Phe | Phe | Glu | Ile | Asp | Leu | Thr | Ser | Arg | Pro | Ala | His |
| | | | | 405 | | | | | 410 | | | | | 415 | |
| Gly | Gly | Lys | Thr | Glu | Gln | Gly | Leu | Ser | Pro | Lys | Ser | Lys | Pro | Phe | Ala |
| | | | 420 | | | | | 425 | | | | | 430 | | |
| Thr | Asp | Ser | Gly | Ala | Met | Ser | His | Lys | Leu | Glu | Lys | Ala | Asp | Leu | Leu |
| | | 435 | | | | | 440 | | | | | 445 | | | |
| Lys | Ala | Ile | Gln | Glu | Gln | Leu | Ile | Ala | Asn | Val | His | Ser | Asn | Asp | Asp |
| | | 450 | | | | | 455 | | | | | 460 | | | |
| Tyr | Phe | Glu | Val | Ile | Asp | Phe | Ala | Ser | Asp | Ala | Thr | Ile | Thr | Asp | Arg |
| 465 | | | | | 470 | | | | | 475 | | | | | 480 |
| Asn | Gly | Lys | Val | Tyr | Phe | Ala | Asp | Lys | Asp | Gly | Ser | Val | Thr | Leu | Pro |
| | | | | 485 | | | | | 490 | | | | | 495 | |

```
Thr Gln Pro Val Gln Glu Phe Leu Leu Ser Gly His Val Arg Val Arg
            500                 505                 510

Tyr Lys Glu Lys Pro Ile Gln Asn Gln Ala Lys Ser Val Asp Val Glu
            515                 520                 525

Tyr Thr Val Gln Phe Thr Pro Leu Asn Pro Asp Asp Phe Arg Pro
    530                 535                 540

Gly Leu Lys Asp Thr Lys Leu Leu Lys Thr Leu Ala Ile Gly Asp Thr
545                 550                 555                 560

Ile Thr Ser Gln Glu Leu Leu Ala Gln Ala Gln Ser Ile Leu Asn Lys
                565                 570                 575

Asn His Pro Gly Tyr Thr Ile Tyr Glu Arg Asp Ser Ser Ile Val Thr
            580                 585                 590

His Asp Asn Asp Ile Phe Arg Thr Ile Leu Pro Met Asp Gln Glu Phe
            595                 600                 605

Thr Tyr Arg Val Lys Asn Arg Glu Gln Ala Tyr Arg Ile Asn Lys Lys
    610                 615                 620

Ser Gly Leu Asn Glu Glu Ile Asn Asn Thr Asp Leu Ile Ser Glu Lys
625                 630                 635                 640

Tyr Tyr Val Leu Lys Lys Gly Glu Lys Pro Tyr Asp Pro Phe Asp Arg
                645                 650                 655

Ser His Leu Lys Leu Phe Thr Ile Lys Tyr Val Asp Val Asp Thr Asn
            660                 665                 670

Glu Leu Leu Lys Ser Glu Gln Leu Leu Thr Ala Ser Glu Arg Asn Leu
            675                 680                 685

Asp Phe Arg Asp Leu Tyr Asp Pro Arg Asp Lys Ala Lys Leu Leu Tyr
    690                 695                 700

Asn Asn Leu Asp Ala Phe Gly Ile Met Asp Tyr Thr Leu Thr Gly Lys
705                 710                 715                 720

Val Glu Asp Asn His Asp Asp Thr Asn Arg Ile Ile Thr Val Tyr Met
                725                 730                 735

Gly Lys Arg Pro Glu Gly Glu Asn Ala Ser Tyr His Leu Ala Tyr Asp
            740                 745                 750

Lys Asp Arg Tyr Thr Glu Glu Glu Arg Glu Val Tyr Ser Tyr Leu Arg
    755                 760                 765

Tyr Thr Gly Thr Pro Ile Pro Asp Asn Pro Asn Asp Lys Asn Asn Ser
    770                 775                 780

Gln Leu Val Val Ser Val Ala Gly Thr Val Glu Gly Thr Asn Gln Asp
785                 790                 795                 800

Ile Ser Leu Lys Phe Phe Glu Ile Asp Leu Thr Ser Arg Pro Ala His
                805                 810                 815

Gly Gly Lys Thr Glu Gln Gly Leu Ser Pro Lys Ser Lys Pro Phe Ala
            820                 825                 830

Thr Asp Ser Gly Ala Met Ser His Lys Leu Glu Lys Ala Asp Leu Leu
            835                 840                 845

Lys Ala Ile Gln Glu Gln Leu Ile Ala Asn Val His Ser Asn Asp Asp
    850                 855                 860

Tyr Phe Glu Val Ile Asp Phe Ala Ser Asp Ala Thr Ile Thr Asp Arg
865                 870                 875                 880

Asn Gly Lys Val Tyr Phe Ala Asp Lys Asp Gly Ser Val Thr Leu Pro
                885                 890                 895

Thr Gln Pro Val Gln Glu Phe Leu Leu Ser Gly His Val Arg Val Arg
            900                 905                 910

Tyr Lys Glu Lys Pro Ile Gln Asn Gln Ala Lys Ser Val Asp Val Glu
```

915                           920                           925

Tyr  Thr  Val  Gln  Phe  Thr  Pro  Leu  Asn  Pro  Asp  Asp  Phe  Arg  Pro
     930                      935                 940

Gly  Leu  Lys  Asp  Thr  Lys  Leu  Leu  Lys  Thr  Leu  Ala  Ile  Gly  Asp  Thr
945                      950                      955                      960

Ile  Thr  Ser  Gln  Glu  Leu  Leu  Ala  Gln  Ala  Gln  Ser  Ile  Leu  Asn  Lys
                         965                      970                 975

Asn  His  Pro  Gly  Tyr  Thr  Ile  Tyr  Glu  Arg  Asp  Ser  Ser  Ile  Val  Thr
               980                      985                      990

His  Asp  Asn  Asp  Ile  Phe  Arg  Thr  Ile  Leu  Pro  Met  Asp  Gln  Glu  Phe
          995                      1000                 1005

Thr  Tyr  Arg  Val  Lys  Asn  Arg  Glu  Gln  Ala  Tyr  Arg  Ile  Asn  Lys  Lys
     1010                     1015                     1020

Ser  Gly  Leu  Asn  Glu  Glu  Ile  Asn  Asn  Thr  Asp  Leu  Ile  Ser  Glu  Lys
1025                     1030                     1035                     1040

Tyr  Tyr  Val  Leu  Lys  Lys  Gly  Glu  Lys  Pro  Tyr  Asp  Pro  Phe  Asp  Arg
                         1045                     1050                1055

Ser  His  Leu  Lys  Leu  Phe  Thr  Ile  Lys  Tyr  Val  Asp  Val  Asp  Thr  Asn
               1060                     1065                     1070

Glu  Leu  Leu  Lys  Ser  Glu  Gln  Leu  Leu  Thr  Ala  Ser  Glu  Arg  Asn  Leu
     1075                     1080                     1085

Asp  Phe  Arg  Asp  Leu  Tyr  Asp  Pro  Arg  Asp  Lys  Ala  Lys  Leu  Leu  Tyr
     1090                     1095                     1100

Asn  Asn  Leu  Asp  Ala  Phe  Gly  Ile  Met  Asp  Tyr  Thr  Leu  Thr  Gly  Lys
1105                     1110                     1115                     1120

Val  Glu  Asp  Asn  His  Asp  Asp  Thr  Asn  Arg  Ile  Ile  Thr  Val  Tyr  Met
                    1125                     1130                     1135

Gly  Lys  Arg  Pro  Glu  Gly  Glu  Asn  Ala  Ser  Tyr  His  Leu  Ala  Tyr  Asp
               1140                     1145                     1150

Lys  Asp  Arg  Tyr  Thr  Glu  Glu  Glu  Arg  Glu  Val  Tyr  Ser  Tyr  Leu  Arg
               1155                     1160                     1165

Tyr  Thr  Gly  Thr  Pro  Ile  Pro  Asp  Asn  Pro  Asn  Asp  Lys
     1170                     1175                     1180

( 2 ) INFORMATION FOR SEQ ID NO:3:

( i ) SEQUENCE CHARACTERISTICS:
        ( A ) LENGTH: 813 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

Ile  Ala  Gly  Pro  Glu  Trp  Leu  Leu  Asp  Arg  Pro  Ser  Val  Asn  Asn  Ser
1                        5                        10                       15

Gln  Leu  Val  Val  Ser  Val  Ala  Gly  Thr  Val  Glu  Gly  Thr  Asn  Gln  Asp
               20                       25                       30

Ile  Ser  Leu  Lys  Phe  Phe  Glu  Ile  Asp  Leu  Thr  Ser  Arg  Pro  Ala  His
               35                       40                       45

Gly  Gly  Lys  Thr  Glu  Gln  Gly  Leu  Ser  Pro  Lys  Ser  Lys  Pro  Phe  Ala
     50                       55                       60

Thr  Asp  Ser  Gly  Ala  Met  Ser  His  Lys  Leu  Glu  Lys  Ala  Asp  Leu  Leu
65                       70                       75                       80

Lys  Ala  Ile  Gln  Glu  Gln  Leu  Ile  Ala  Asn  Val  His  Ser  Asn  Asp  Asp
                    85                       90                       95

```
Tyr  Phe  Glu  Val  Ile  Asp  Phe  Ala  Ser  Asp  Ala  Thr  Ile  Thr  Asp  Arg
               100                 105                      110

Asn  Gly  Lys  Val  Tyr  Phe  Ala  Asp  Lys  Asp  Gly  Ser  Val  Thr  Leu  Pro
          115                 120                      125

Thr  Gln  Pro  Val  Gln  Glu  Phe  Leu  Leu  Ser  Gly  His  Val  Arg  Val  Arg
     130                 135                      140

Tyr  Lys  Glu  Lys  Pro  Ile  Gln  Asn  Gln  Ala  Lys  Ser  Val  Asp  Val  Glu
145                      150                 155                           160

Tyr  Thr  Val  Gln  Phe  Thr  Pro  Leu  Asn  Pro  Asp  Asp  Phe  Arg  Pro
                    165                 170                      175

Gly  Leu  Lys  Asp  Thr  Lys  Leu  Leu  Lys  Thr  Leu  Ala  Ile  Gly  Asp  Thr
               180                 185                           190

Ile  Thr  Ser  Gln  Glu  Leu  Leu  Ala  Gln  Ala  Gln  Ser  Ile  Leu  Asn  Lys
          195                      200                 205

Asn  His  Pro  Gly  Tyr  Thr  Ile  Tyr  Glu  Arg  Asp  Ser  Ser  Ile  Val  Thr
     210                      215                      220

His  Asp  Asn  Asp  Ile  Phe  Arg  Thr  Ile  Leu  Pro  Met  Asp  Gln  Glu  Phe
225                      230                 235                           240

Thr  Tyr  Arg  Val  Lys  Asn  Arg  Glu  Gln  Ala  Tyr  Arg  Ile  Asn  Lys  Lys
               245                      250                           255

Ser  Gly  Leu  Asn  Glu  Glu  Ile  Asn  Asn  Thr  Asp  Leu  Ile  Ser  Glu  Lys
               260                 265                      270

Tyr  Tyr  Val  Leu  Lys  Lys  Gly  Glu  Lys  Pro  Tyr  Asp  Pro  Phe  Asp  Arg
          275                      280                 285

Ser  His  Leu  Lys  Leu  Phe  Thr  Ile  Lys  Tyr  Val  Asp  Val  Asp  Thr  Asn
     290                      295                 300

Glu  Leu  Leu  Lys  Ser  Glu  Gln  Leu  Leu  Thr  Ala  Ser  Glu  Arg  Asn  Leu
305                      310                      315                      320

Asp  Phe  Arg  Asp  Leu  Tyr  Asp  Pro  Arg  Asp  Lys  Ala  Lys  Leu  Leu  Tyr
                    325                      330                      335

Asn  Asn  Leu  Asp  Ala  Phe  Gly  Ile  Met  Asp  Tyr  Thr  Leu  Thr  Gly  Lys
               340                      345                      350

Val  Glu  Asp  Asn  His  Asp  Asp  Thr  Asn  Arg  Ile  Ile  Thr  Val  Tyr  Met
          355                      360                      365

Gly  Lys  Arg  Pro  Glu  Gly  Glu  Asn  Ala  Ser  Tyr  His  Leu  Ala  Tyr  Asp
     370                      375                      380

Lys  Asp  Arg  Tyr  Thr  Glu  Glu  Glu  Arg  Glu  Val  Tyr  Ser  Tyr  Leu  Arg
385                      390                      395                      400

Tyr  Thr  Gly  Thr  Pro  Ile  Pro  Asp  Asn  Pro  Asn  Asp  Lys  Asn  Asn  Ser
                    405                      410                      415

Gln  Leu  Val  Val  Ser  Val  Ala  Gly  Thr  Val  Glu  Gly  Thr  Asn  Gln  Asp
               420                      425                      430

Ile  Ser  Leu  Lys  Phe  Phe  Glu  Ile  Asp  Leu  Thr  Ser  Arg  Pro  Ala  His
          435                      440                      445

Gly  Gly  Lys  Thr  Glu  Gln  Gly  Leu  Ser  Pro  Lys  Ser  Lys  Pro  Phe  Ala
     450                      455                      460

Thr  Asp  Ser  Gly  Ala  Met  Ser  His  Lys  Leu  Glu  Lys  Ala  Asp  Leu  Leu
465                      470                      475                      480

Lys  Ala  Ile  Gln  Glu  Gln  Leu  Ile  Ala  Asn  Val  His  Ser  Asn  Asp
               485                      490                      495

Tyr  Phe  Glu  Val  Ile  Asp  Phe  Ala  Ser  Asp  Ala  Thr  Ile  Thr  Asp  Arg
               500                 505                      510

Asn  Gly  Lys  Val  Tyr  Phe  Ala  Asp  Lys  Asp  Gly  Ser  Val  Thr  Leu  Pro
```

|     |     | 515 |     |     |     | 520 |     |     |     | 525 |     |     |     |
| --- | --- | --- | --- | --- | --- | --- | --- | --- | --- | --- | --- | --- | --- |
| Thr | Gln | Pro | Val | Gln | Glu | Phe | Leu | Leu | Ser | Gly | His | Val | Arg | Val | Arg |
|     | 530 |     |     |     |     | 535 |     |     |     |     | 540 |     |     |     |
| Tyr | Lys | Glu | Lys | Pro | Ile | Gln | Asn | Gln | Ala | Lys | Ser | Val | Asp | Val | Glu |
| 545 |     |     |     |     | 550 |     |     |     |     | 555 |     |     |     |     | 560 |
| Tyr | Thr | Val | Gln | Phe | Thr | Pro | Leu | Asn | Pro | Asp | Asp | Phe | Arg | Pro |
|     |     |     |     | 565 |     |     |     |     | 570 |     |     |     | 575 |     |
| Gly | Leu | Lys | Asp | Thr | Lys | Leu | Leu | Lys | Thr | Leu | Ala | Ile | Gly | Asp | Thr |
|     |     |     | 580 |     |     |     |     | 585 |     |     |     |     | 590 |     |     |
| Ile | Thr | Ser | Gln | Glu | Leu | Leu | Ala | Gln | Ala | Gln | Ser | Ile | Leu | Asn | Lys |
|     |     | 595 |     |     |     |     | 600 |     |     |     |     | 605 |     |     |     |
| Asn | His | Pro | Gly | Tyr | Thr | Ile | Tyr | Glu | Arg | Asp | Ser | Ser | Ile | Val | Thr |
|     | 610 |     |     |     |     | 615 |     |     |     |     | 620 |     |     |     |     |
| His | Asp | Asn | Asp | Ile | Phe | Arg | Thr | Ile | Leu | Pro | Met | Asp | Gln | Glu | Phe |
| 625 |     |     |     |     | 630 |     |     |     |     | 635 |     |     |     |     | 640 |
| Thr | Tyr | Arg | Val | Lys | Asn | Arg | Gln | Gln | Ala | Tyr | Arg | Ile | Asn | Lys | Lys |
|     |     |     |     | 645 |     |     |     |     | 650 |     |     |     |     | 655 |     |
| Ser | Gly | Leu | Asn | Glu | Glu | Ile | Asn | Asn | Thr | Asp | Leu | Ile | Ser | Glu | Lys |
|     |     |     | 660 |     |     |     |     | 665 |     |     |     |     | 670 |     |     |
| Tyr | Tyr | Val | Leu | Lys | Lys | Gly | Glu | Lys | Pro | Tyr | Asp | Pro | Phe | Asp | Arg |
|     |     | 675 |     |     |     |     | 680 |     |     |     |     | 685 |     |     |     |
| Ser | His | Leu | Lys | Leu | Phe | Thr | Ile | Lys | Tyr | Val | Asp | Val | Asp | Thr | Asn |
|     | 690 |     |     |     |     | 695 |     |     |     |     | 700 |     |     |     |     |
| Glu | Leu | Leu | Lys | Ser | Glu | Gln | Leu | Leu | Thr | Ala | Ser | Glu | Arg | Asn | Leu |
| 705 |     |     |     |     | 710 |     |     |     |     | 715 |     |     |     |     | 720 |
| Asp | Phe | Arg | Asp | Leu | Tyr | Asp | Pro | Arg | Asp | Lys | Ala | Lys | Leu | Leu | Tyr |
|     |     |     |     | 725 |     |     |     |     | 730 |     |     |     |     | 735 |     |
| Asn | Asn | Leu | Asp | Ala | Phe | Gly | Ile | Met | Asp | Tyr | Thr | Leu | Thr | Gly | Lys |
|     |     |     | 740 |     |     |     |     | 745 |     |     |     |     | 750 |     |     |
| Val | Glu | Asp | Asn | His | Asp | Asp | Thr | Asn | Arg | Ile | Ile | Thr | Val | Tyr | Met |
|     |     | 755 |     |     |     |     | 760 |     |     |     |     | 765 |     |     |     |
| Gly | Lys | Arg | Pro | Glu | Gly | Glu | Asn | Ala | Ser | Tyr | His | Leu | Ala | Tyr | Asp |
|     | 770 |     |     |     |     | 775 |     |     |     |     | 780 |     |     |     |     |
| Lys | Asp | Arg | Tyr | Thr | Glu | Glu | Glu | Arg | Glu | Val | Tyr | Ser | Tyr | Leu | Arg |
| 785 |     |     |     |     | 790 |     |     |     |     | 795 |     |     |     |     | 800 |
| Tyr | Thr | Gly | Thr | Pro | Ile | Pro | Asp | Asn | Pro | Asn | Asp | Lys |
|     |     |     |     | 805 |     |     |     |     | 810 |     |     |     |

( 2 ) INFORMATION FOR SEQ ID NO:4:

( i ) SEQUENCE CHARACTERISTICS:
        ( A ) LENGTH: 800 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:4:

| Asn | Asn | Ser | Gln | Leu | Val | Val | Ser | Val | Ala | Gly | Thr | Val | Glu | Gly | Thr |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asn | Gln | Asp | Ile | Ser | Leu | Lys | Phe | Phe | Glu | Ile | Asp | Leu | Thr | Ser | Arg |
|     |     |     | 20  |     |     |     |     | 25  |     |     |     |     | 30  |     |     |
| Pro | Ala | His | Gly | Gly | Lys | Thr | Glu | Gln | Gly | Leu | Ser | Pro | Lys | Ser | Lys |
|     |     | 35  |     |     |     |     | 40  |     |     |     |     | 45  |     |     |     |
| Pro | Phe | Ala | Thr | Asp | Ser | Gly | Ala | Met | Ser | His | Lys | Leu | Glu | Lys | Ala |
|     |     | 50  |     |     |     |     | 55  |     |     |     |     | 60  |     |     |     |

```
Asp  Leu  Leu  Lys  Ala  Ile  Gln  Glu  Gln  Leu  Ile  Ala  Asn  Val  His  Ser
 65                      70                       75                       80

Asn  Asp  Asp  Tyr  Phe  Glu  Val  Ile  Asp  Phe  Ala  Ser  Asp  Ala  Thr  Ile
                         85                       90                       95

Thr  Asp  Arg  Asn  Gly  Lys  Val  Tyr  Phe  Ala  Asp  Lys  Asp  Gly  Ser  Val
                   100                      105                      110

Thr  Leu  Pro  Thr  Gln  Pro  Val  Gln  Glu  Phe  Leu  Leu  Ser  Gly  His  Val
                   115                      120                      125

Arg  Val  Arg  Tyr  Lys  Glu  Lys  Pro  Ile  Gln  Asn  Gln  Ala  Lys  Ser  Val
          130                      135                      140

Asp  Val  Glu  Tyr  Thr  Val  Gln  Phe  Thr  Pro  Leu  Asn  Pro  Asp  Asp  Asp
145                      150                      155                      160

Phe  Arg  Pro  Gly  Leu  Lys  Asp  Thr  Lys  Leu  Leu  Lys  Thr  Leu  Ala  Ile
                        165                      170                      175

Gly  Asp  Thr  Ile  Thr  Ser  Gln  Glu  Leu  Leu  Ala  Gln  Ala  Gln  Ser  Ile
                   180                      185                      190

Leu  Asn  Lys  Asn  His  Pro  Gly  Tyr  Thr  Ile  Tyr  Glu  Arg  Asp  Ser  Ser
               195                      200                      205

Ile  Val  Thr  His  Asp  Asn  Asp  Ile  Phe  Arg  Thr  Ile  Leu  Pro  Met  Asp
          210                      215                      220

Gln  Glu  Phe  Thr  Tyr  Arg  Val  Lys  Asn  Arg  Glu  Gln  Ala  Tyr  Arg  Ile
225                      230                      235                      240

Asn  Lys  Lys  Ser  Gly  Leu  Asn  Glu  Glu  Ile  Asn  Asn  Thr  Asp  Leu  Ile
                        245                      250                      255

Ser  Glu  Lys  Tyr  Tyr  Val  Leu  Lys  Lys  Gly  Glu  Lys  Pro  Tyr  Asp  Pro
                   260                      265                      270

Phe  Asp  Arg  Ser  His  Leu  Lys  Leu  Phe  Thr  Ile  Lys  Tyr  Val  Asp  Val
          275                      280                      285

Asp  Thr  Asn  Glu  Leu  Leu  Lys  Ser  Glu  Gln  Leu  Leu  Thr  Ala  Ser  Glu
     290                      295                      300

Arg  Asn  Leu  Asp  Phe  Arg  Asp  Leu  Tyr  Asp  Pro  Arg  Asp  Lys  Ala  Lys
305                      310                      315                      320

Leu  Leu  Tyr  Asn  Asn  Leu  Asp  Ala  Phe  Gly  Ile  Met  Asp  Tyr  Thr  Leu
                        325                      330                      335

Thr  Gly  Lys  Val  Glu  Asp  Asn  His  Asp  Thr  Asn  Arg  Ile  Ile  Thr
                   340                      345                      350

Val  Tyr  Met  Gly  Lys  Arg  Pro  Glu  Gly  Glu  Asn  Ala  Ser  Tyr  His  Leu
          355                      360                      365

Ala  Tyr  Asp  Lys  Asp  Arg  Tyr  Thr  Glu  Glu  Glu  Arg  Glu  Val  Tyr  Ser
     370                      375                      380

Tyr  Leu  Arg  Tyr  Thr  Gly  Thr  Pro  Ile  Pro  Asp  Asn  Pro  Asn  Asp  Lys
385                      390                      395                      400

Asn  Asn  Ser  Gln  Leu  Val  Val  Ser  Val  Ala  Gly  Thr  Val  Glu  Gly  Thr
                        405                      410                      415

Asn  Gln  Asp  Ile  Ser  Leu  Lys  Phe  Phe  Glu  Ile  Asp  Leu  Thr  Ser  Arg
                   420                      425                      430

Pro  Ala  His  Gly  Gly  Lys  Thr  Glu  Gln  Gly  Leu  Ser  Pro  Lys  Ser  Lys
          435                      440                      445

Pro  Phe  Ala  Thr  Asp  Ser  Gly  Ala  Met  Ser  His  Lys  Leu  Glu  Lys  Ala
     450                      455                      460

Asp  Leu  Leu  Lys  Ala  Ile  Gln  Glu  Gln  Leu  Ile  Ala  Asn  Val  His  Ser
465                      470                      475                      480

Asn  Asp  Asp  Tyr  Phe  Glu  Val  Ile  Asp  Phe  Ala  Ser  Asp  Ala  Thr  Ile
```

|     |     |     |     | 485 |     |     |     | 490 |     |     |     | 495 |     |     |
| --- | --- | --- | --- | --- | --- | --- | --- | --- | --- | --- | --- | --- | --- | --- |
| Thr | Asp | Arg | Asn | Gly | Lys | Val | Tyr | Phe | Ala | Asp | Lys | Asp | Ser | Val |
|     |     |     | 500 |     |     |     |     | 505 |     |     |     | 510 |     |     |
| Thr | Leu | Pro | Thr | Gln | Pro | Val | Gln | Glu | Phe | Leu | Leu | Ser | Gly | His | Val |
|     |     |     | 515 |     |     |     |     | 520 |     |     |     | 525 |     |     |
| Arg | Val | Arg | Tyr | Lys | Glu | Lys | Pro | Ile | Gln | Asn | Gln | Ala | Lys | Ser | Val |
|     |     | 530 |     |     |     | 535 |     |     |     |     | 540 |     |     |     |
| Asp | Val | Glu | Tyr | Thr | Val | Gln | Phe | Thr | Pro | Leu | Asn | Pro | Asp | Asp |
| 545 |     |     |     |     | 550 |     |     |     |     | 555 |     |     |     | 560 |
| Phe | Arg | Pro | Gly | Leu | Lys | Asp | Thr | Lys | Leu | Leu | Lys | Thr | Leu | Ala | Ile |
|     |     |     |     | 565 |     |     |     |     | 570 |     |     |     |     | 575 |
| Gly | Asp | Thr | Ile | Thr | Ser | Gln | Glu | Leu | Leu | Ala | Gln | Ala | Gln | Ser | Ile |
|     |     |     | 580 |     |     |     |     | 585 |     |     |     |     | 590 |     |
| Leu | Asn | Lys | Asn | His | Pro | Gly | Tyr | Thr | Ile | Tyr | Glu | Arg | Asp | Ser | Ser |
|     |     | 595 |     |     |     |     | 600 |     |     |     |     | 605 |     |     |
| Ile | Val | Thr | His | Asp | Asn | Asp | Ile | Phe | Arg | Thr | Ile | Leu | Pro | Met | Asp |
|     | 610 |     |     |     |     | 615 |     |     |     |     | 620 |     |     |     |
| Gln | Glu | Phe | Thr | Tyr | Arg | Val | Lys | Asn | Arg | Glu | Gln | Ala | Tyr | Arg | Ile |
| 625 |     |     |     |     | 630 |     |     |     |     | 635 |     |     |     |     | 640 |
| Asn | Lys | Lys | Ser | Gly | Leu | Asn | Glu | Glu | Ile | Asn | Asn | Thr | Asp | Leu | Ile |
|     |     |     |     | 645 |     |     |     |     | 650 |     |     |     |     | 655 |
| Ser | Glu | Lys | Tyr | Tyr | Val | Leu | Lys | Lys | Gly | Glu | Lys | Pro | Tyr | Asp | Pro |
|     |     |     | 660 |     |     |     |     | 665 |     |     |     | 670 |     |     |
| Phe | Asp | Arg | Ser | His | Leu | Lys | Leu | Phe | Thr | Ile | Lys | Tyr | Val | Asp | Val |
|     |     |     | 675 |     |     |     |     | 680 |     |     |     | 685 |     |     |
| Asp | Thr | Asn | Glu | Leu | Leu | Lys | Ser | Glu | Gln | Leu | Leu | Thr | Ala | Ser | Glu |
|     | 690 |     |     |     |     | 695 |     |     |     |     | 700 |     |     |     |
| Arg | Asn | Leu | Asp | Phe | Arg | Asp | Leu | Tyr | Asp | Pro | Arg | Asp | Lys | Ala | Lys |
| 705 |     |     |     |     | 710 |     |     |     |     | 715 |     |     |     |     | 720 |
| Leu | Leu | Tyr | Asn | Asn | Leu | Asp | Ala | Phe | Gly | Ile | Met | Asp | Tyr | Thr | Leu |
|     |     |     |     | 725 |     |     |     |     | 730 |     |     |     |     | 735 |
| Thr | Gly | Lys | Val | Glu | Asp | Asn | His | Asp | Asp | Thr | Asn | Arg | Ile | Ile | Thr |
|     |     |     | 740 |     |     |     |     | 745 |     |     |     |     | 750 |     |
| Val | Tyr | Met | Gly | Lys | Arg | Pro | Glu | Gly | Glu | Asn | Ala | Ser | Tyr | His | Leu |
|     |     | 755 |     |     |     |     | 760 |     |     |     |     | 765 |     |     |
| Ala | Tyr | Asp | Lys | Asp | Arg | Tyr | Thr | Glu | Glu | Glu | Arg | Glu | Val | Tyr | Ser |
|     | 770 |     |     |     |     | 775 |     |     |     |     | 780 |     |     |     |
| Tyr | Leu | Arg | Tyr | Thr | Gly | Thr | Pro | Ile | Pro | Asp | Asn | Pro | Asn | Asp | Lys |
| 785 |     |     |     |     | 790 |     |     |     |     | 795 |     |     |     |     | 800 |

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

GCTGCTAGAC GCGCCATCTG TCAAC    25

( 2 ) INFORMATION FOR SEQ ID NO:6:

( i ) SEQUENCE CHARACTERISTICS:
        ( A ) LENGTH: 23 base pairs
        ( B ) TYPE: nucleic acid ( C ) STRANDEDNESS: double
( D ) TOPOLOGY: linear ( i i ) MOLECULE TYPE: DNA (genomic)

( x i ) SEQUENCE DESCRIPTION: SEQ ID NO:6:

TGGCGCGTCT AGCAGCCACT CAG                23

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

CAAGACATTA GTCTGGCCTT TTTTGAAATC G                31

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

GGCCAGACTA ATGTCTTGAT TCG                23

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

CGATCTAACA TCGGCGCCTG CTCATGG                27

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

CGCCGATGTT AGATCGATTT C                21

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

GCTCATGGAG GCGCCACAGA GGGC 24

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

GGCGCCTCCA TGAGCAGGTC 20

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

GCTTAAGTCC GGCCTCAAAA CCATTTGC 28

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

TGAGGCCGGA CTTAAGCCTT GCTC 24

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

GCCGATCGAT ATACCGAAGA AGAACGAG 28

( 2 ) INFORMATION FOR SEQ ID NO:16:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

TATCGATCGG CATCATAGGC TAAATGATAG C 31

( 2 ) INFORMATION FOR SEQ ID NO:17:

( i ) SEQUENCE CHARACTERISTICS:
        ( A ) LENGTH: 1194 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:17:

```
Met  Lys  Thr  Glu  Glu  Gly  Lys  Leu  Val  Ile  Trp  Ile  Asn  Gly  Asp  Lys
 1                    5                        10                       15

Gly  Tyr  Asn  Gly  Leu  Ala  Glu  Val  Gly  Lys  Lys  Phe  Glu  Lys  Asp  Thr
               20                       25                       30

Gly  Ile  Lys  Val  Thr  Val  Glu  His  Pro  Asp  Lys  Leu  Glu  Glu  Lys  Phe
          35                       40                       45

Pro  Gln  Val  Ala  Ala  Thr  Gly  Asp  Gly  Pro  Asp  Ile  Ile  Phe  Trp  Ala
     50                       55                       60

His  Asp  Arg  Phe  Gly  Gly  Tyr  Ala  Gln  Ser  Gly  Leu  Leu  Ala  Glu  Ile
65                        70                       75                         80

Thr  Pro  Asp  Lys  Ala  Phe  Gln  Asp  Lys  Leu  Tyr  Pro  Phe  Thr  Trp  Asp
               85                       90                       95

Ala  Val  Arg  Tyr  Asn  Gly  Lys  Leu  Ile  Ala  Tyr  Pro  Ile  Ala  Val  Glu
              100                      105                      110

Ala  Leu  Ser  Leu  Ile  Tyr  Asn  Lys  Asp  Leu  Leu  Pro  Asn  Pro  Pro  Lys
              115                      120                      125

Thr  Trp  Glu  Glu  Ile  Pro  Ala  Leu  Asp  Lys  Glu  Leu  Lys  Ala  Lys  Gly
         130                      135                      140

Lys  Ser  Ala  Leu  Met  Phe  Asn  Leu  Gln  Glu  Pro  Tyr  Phe  Thr  Trp  Pro
145                      150                      155                      160

Leu  Ile  Ala  Ala  Asp  Gly  Gly  Tyr  Ala  Phe  Lys  Tyr  Glu  Asn  Gly  Lys
                   165                      170                      175

Tyr  Asp  Ile  Lys  Asp  Val  Gly  Val  Asp  Asn  Ala  Gly  Ala  Lys  Ala  Gly
              180                      185                      190

Leu  Thr  Phe  Leu  Val  Asp  Leu  Ile  Lys  Asn  Lys  His  Met  Asn  Ala  Asp
         195                      200                      205

Thr  Asp  Tyr  Ser  Ile  Ala  Glu  Ala  Ala  Phe  Asn  Lys  Gly  Glu  Thr  Ala
    210                      215                      220

Met  Thr  Ile  Asn  Gly  Pro  Trp  Ala  Trp  Ser  Asn  Ile  Asp  Thr  Ser  Lys
225                      230                      235                      240

Val  Asn  Tyr  Gly  Val  Thr  Val  Leu  Pro  Thr  Phe  Lys  Gly  Gln  Pro  Ser
                    245                      250                      255

Lys  Pro  Phe  Val  Gly  Val  Leu  Ser  Ala  Gly  Ile  Asn  Ala  Ala  Ser  Pro
              260                      265                      270

Asn  Lys  Glu  Leu  Ala  Lys  Glu  Phe  Leu  Glu  Asn  Tyr  Leu  Leu  Thr  Asp
         275                      280                      285

Glu  Gly  Leu  Glu  Ala  Val  Asn  Lys  Asp  Lys  Pro  Leu  Gly  Ala  Val  Ala
    290                      295                      300

Leu  Lys  Ser  Tyr  Glu  Glu  Leu  Ala  Lys  Asp  Pro  Arg  Ile  Ala  Ala
305                      310                      315                      320

Thr  Met  Glu  Asn  Ala  Gln  Lys  Gly  Glu  Ile  Met  Pro  Asn  Ile  Pro  Gln
              325                      330                      335

Met  Ser  Ala  Phe  Trp  Tyr  Ala  Val  Arg  Thr  Ala  Val  Ile  Asn  Ala  Ala
                  340                      345                      350

Ser  Gly  Arg  Gln  Thr  Val  Asp  Glu  Ala  Leu  Lys  Asp  Ala  Gln  Thr  Asn
              355                      360                      365
```

-continued

| | | | | | | | | | | | | | |
|---|---|---|---|---|---|---|---|---|---|---|---|---|---|
| Ser | Ser | Ser | Val | Pro | Gly | Arg | Gly | Ser | Ile | Glu | Gly | Arg | Ile | Ala | Gly |
| | 370 | | | | 375 | | | | | 380 | | | |
| Pro | Glu | Trp | Leu | Leu | Asp | Ala | Pro | Ser | Val | Asn | Asn | Ser | Gln | Leu | Val |
| 385 | | | | | 390 | | | | 395 | | | | | 400 |
| Val | Ser | Val | Ala | Gly | Thr | Val | Glu | Gly | Thr | Asn | Gln | Asp | Ile | Ser | Leu |
| | | | | 405 | | | | | 410 | | | | | 415 |
| Ala | Phe | Phe | Glu | Ile | Asp | Leu | Thr | Ser | Ala | Pro | Ala | His | Gly | Gly | Ala |
| | | | 420 | | | | | 425 | | | | 430 | |
| Thr | Glu | Gln | Gly | Leu | Ser | Pro | Ala | Ser | Lys | Pro | Phe | Ala | Thr | Asp | Ser |
| | | | 435 | | | | 440 | | | | | 445 | | |
| Gly | Ala | Met | Ser | His | Lys | Leu | Glu | Lys | Ala | Asp | Leu | Leu | Lys | Ala | Ile |
| | 450 | | | | | 455 | | | | 460 | | | |
| Gln | Glu | Gln | Leu | Ile | Ala | Asn | Val | His | Ser | Asn | Asp | Asp | Tyr | Phe | Glu |
| 465 | | | | | 470 | | | | 475 | | | | | 480 |
| Val | Ile | Asp | Phe | Ala | Ser | Asp | Ala | Thr | Ile | Thr | Asp | Arg | Asn | Gly | Lys |
| | | | | 485 | | | | | 490 | | | | | 495 |
| Val | Tyr | Phe | Ala | Asp | Lys | Asp | Gly | Ser | Val | Thr | Leu | Pro | Thr | Gln | Pro |
| | | | 500 | | | | | 505 | | | | 510 | | |
| Val | Gln | Glu | Phe | Leu | Leu | Ser | Gly | His | Val | Arg | Val | Arg | Tyr | Lys | Glu |
| | | | 515 | | | | | 520 | | | | 525 | | |
| Lys | Pro | Ile | Gln | Asn | Gln | Ala | Lys | Ser | Val | Asp | Val | Glu | Tyr | Thr | Val |
| | 530 | | | | | 535 | | | | 540 | | | |
| Gln | Phe | Thr | Pro | Leu | Asn | Pro | Asp | Asp | Phe | Arg | Pro | Gly | Leu | Lys |
| 545 | | | | | 550 | | | | | 555 | | | | 560 |
| Asp | Thr | Lys | Leu | Leu | Lys | Thr | Leu | Ala | Ile | Gly | Asp | Thr | Ile | Thr | Ser |
| | | | | 565 | | | | | 570 | | | | 575 |
| Gln | Glu | Leu | Leu | Ala | Gln | Ala | Gln | Ser | Ile | Leu | Asn | Lys | Asn | His | Pro |
| | | | 580 | | | | | 585 | | | | | 590 |
| Gly | Tyr | Thr | Ile | Tyr | Glu | Arg | Asp | Ser | Ser | Ile | Val | Thr | His | Asp | Asn |
| | | | 595 | | | | 600 | | | | | 605 | |
| Asp | Ile | Phe | Arg | Thr | Ile | Leu | Pro | Met | Asp | Gln | Glu | Phe | Thr | Tyr | Arg |
| | 610 | | | | | 615 | | | | 620 | | | |
| Val | Lys | Asn | Arg | Glu | Gln | Ala | Tyr | Arg | Ile | Asn | Lys | Lys | Ser | Gly | Leu |
| 625 | | | | | 630 | | | | 635 | | | | 640 |
| Asn | Glu | Glu | Ile | Asn | Asn | Thr | Asp | Leu | Ile | Ser | Glu | Lys | Tyr | Tyr | Val |
| | | | | 645 | | | | | 650 | | | | 655 |
| Leu | Lys | Lys | Gly | Glu | Lys | Pro | Tyr | Asp | Pro | Phe | Asp | Arg | Ser | His | Leu |
| | | | 660 | | | | 665 | | | | | 670 | |
| Lys | Leu | Phe | Thr | Ile | Lys | Tyr | Val | Asp | Val | Asp | Thr | Asn | Glu | Leu | Leu |
| | | | 675 | | | | | 680 | | | | 685 | | |
| Lys | Ser | Glu | Gln | Leu | Leu | Thr | Ala | Ser | Glu | Arg | Asn | Leu | Asp | Phe | Arg |
| | 690 | | | | | 695 | | | | 700 | | | |
| Asp | Leu | Tyr | Asp | Pro | Arg | Asp | Lys | Ala | Lys | Leu | Leu | Tyr | Asn | Asn | Leu |
| 705 | | | | | 710 | | | | 715 | | | | 720 |
| Asp | Ala | Phe | Gly | Ile | Met | Asp | Tyr | Thr | Leu | Thr | Gly | Lys | Val | Glu | Asp |
| | | | | 725 | | | | | 730 | | | | 735 |
| Asn | His | Asp | Asp | Thr | Asn | Arg | Ile | Ile | Thr | Val | Tyr | Met | Gly | Lys | Arg |
| | | | 740 | | | | | 745 | | | | 750 | | |
| Pro | Glu | Gly | Glu | Asn | Ala | Ser | Tyr | His | Leu | Ala | Tyr | Asp | Lys | Asp | Arg |
| | | 755 | | | | | 760 | | | | 765 | | |
| Tyr | Thr | Glu | Glu | Glu | Arg | Glu | Val | Tyr | Ser | Tyr | Leu | Arg | Tyr | Thr | Gly |
| | 770 | | | | | 775 | | | | 780 | | | |
| Thr | Pro | Ile | Pro | Asp | Asn | Pro | Asn | Asp | Lys | Asn | Asn | Ser | Gln | Leu | Val |

```
785                 790                 795                 800
Val Ser Val Ala Gly Thr Val Glu Gly Thr Asn Gln Asp Ile Ser Leu
                    805                 810                 815
Lys Phe Phe Glu Ile Asp Leu Thr Ser Arg Pro Ala His Gly Gly Lys
                    820                 825                 830
Thr Glu Gln Gly Leu Ser Pro Lys Ser Lys Pro Phe Ala Thr Asp Ser
                    835                 840                 845
Gly Ala Met Ser His Lys Leu Glu Lys Ala Asp Leu Leu Lys Ala Ile
                    850                 855                 860
Gln Glu Gln Leu Ile Ala Asn Val His Ser Asn Asp Asp Tyr Phe Glu
865                 870                 875                 880
Val Ile Asp Phe Ala Ser Asp Ala Thr Ile Thr Asp Arg Asn Gly Lys
                    885                 890                 895
Val Tyr Phe Ala Asp Lys Asp Gly Ser Val Thr Leu Pro Thr Gln Pro
                    900                 905                 910
Val Gln Glu Phe Leu Leu Ser Gly His Val Arg Val Arg Tyr Lys Glu
                    915                 920                 925
Lys Pro Ile Gln Asn Gln Ala Lys Ser Val Asp Val Glu Tyr Thr Val
                    930                 935                 940
Gln Phe Thr Pro Leu Asn Pro Asp Asp Phe Arg Pro Gly Leu Lys
945                 950                 955                 960
Asp Thr Lys Leu Leu Lys Thr Leu Ala Ile Gly Asp Thr Ile Thr Ser
                    965                 970                 975
Gln Glu Leu Leu Ala Gln Ala Gln Ser Ile Leu Asn Lys Asn His Pro
                    980                 985                 990
Gly Tyr Thr Ile Tyr Glu Arg Asp Ser Ser Ile Val Thr His Asp Asn
                    995                 1000                1005
Asp Ile Phe Arg Thr Ile Leu Pro Met Asp Gln Glu Phe Thr Tyr Arg
                    1010                1015                1020
Val Lys Asn Arg Glu Gln Ala Tyr Arg Ile Asn Lys Lys Ser Gly Leu
1025                1030                1035                1040
Asn Glu Glu Ile Asn Asn Thr Asp Leu Ile Ser Glu Lys Tyr Tyr Val
                    1045                1050                1055
Leu Lys Lys Gly Glu Lys Pro Tyr Asp Pro Phe Asp Arg Ser His Leu
                    1060                1065                1070
Lys Leu Phe Thr Ile Lys Tyr Val Asp Val Asp Thr Asn Glu Leu Leu
                    1075                1080                1085
Lys Ser Glu Gln Leu Leu Thr Ala Ser Glu Arg Asn Leu Asp Phe Arg
                    1090                1095                1100
Asp Leu Tyr Asp Pro Arg Asp Lys Ala Lys Leu Leu Tyr Asn Asn Leu
1105                1110                1115                1120
Asp Ala Phe Gly Ile Met Asp Tyr Thr Leu Thr Gly Lys Val Glu Asp
                    1125                1130                1135
Asn His Asp Asp Thr Asn Arg Ile Ile Thr Val Tyr Met Gly Lys Arg
                    1140                1145                1150
Pro Glu Gly Glu Asn Ala Ser Tyr His Leu Ala Tyr Asp Lys Asp Arg
                    1155                1160                1165
Tyr Thr Glu Glu Glu Arg Glu Val Tyr Ser Tyr Leu Arg Tyr Thr Gly
                    1170                1175                1180
Thr Pro Ile Pro Asp Asn Pro Asn Asp Lys
1185                1190
```

( 2 ) INFORMATION FOR SEQ ID NO:18:

(i) SEQUENCE CHARACTERISTICS:
  (A) LENGTH: 1194 amino acids
  (B) TYPE: amino acid
  (C) STRANDEDNESS: Not Relevant
  (D) TOPOLOGY: linear (ii) MOLECULE TYPE: protein (xi) SEQUENCE DESCRIPTION: SEQ ID NO:18:

```
Met Lys Thr Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
               100                 105                 110

Ala Leu Ser Leu Ile Tyr Asn Lys Asp Leu Leu Pro Asn Pro Pro Lys
           115                 120                 125

Thr Trp Glu Glu Ile Pro Ala Leu Asp Lys Glu Leu Lys Ala Lys Gly
       130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Val Pro Gly Arg Gly Ser Ile Glu Gly Arg Ile Ala Gly
```

-continued

|  | 370 |  |  |  | 375 |  |  |  |  | 380 |  |  |  |
|---|---|---|---|---|---|---|---|---|---|---|---|---|---|
| Pro 385 | Glu | Trp | Leu | Leu 390 | Asp | Ala | Pro | Ser | Val 395 | Asn | Ser | Gln | Leu | Val 400 |
| Val | Ser | Val | Ala | Gly 405 | Thr | Val | Glu | Gly | Thr 410 | Asn | Gln | Asp | Ile | Ser 415 | Leu |
| Ala | Phe | Phe | Glu 420 | Ile | Asp | Leu | Thr | Ser 425 | Ala | Pro | Ala | His | Gly 430 | Gly | Ala |
| Thr | Glu | Gln 435 | Gly | Leu | Ser | Pro | Ala 440 | Ser | Lys | Pro | Phe | Ala 445 | Thr | Asp | Ser |
| Gly | Ala 450 | Met | Ser | His | Lys | Leu 455 | Glu | Lys | Ala | Asp | Leu 460 | Leu | Lys | Ala | Ile |
| Gln 465 | Glu | Gln | Leu | Ile | Ala 470 | Asn | Val | His | Ser | Asn 475 | Asp | Asp | Tyr | Phe | Glu 480 |
| Val | Ile | Asp | Phe | Ala 485 | Ser | Asp | Ala | Thr | Ile 490 | Thr | Asp | Arg | Asn | Gly 495 | Lys |
| Val | Tyr | Phe | Ala 500 | Asp | Lys | Asp | Gly | Ser 505 | Val | Thr | Leu | Pro | Thr 510 | Gln | Pro |
| Val | Gln | Glu 515 | Phe | Leu | Leu | Ser | Gly 520 | His | Val | Arg | Val | Arg 525 | Tyr | Lys | Glu |
| Lys | Pro 530 | Ile | Gln | Asn | Gln | Ala 535 | Lys | Ser | Val | Asp | Val 540 | Glu | Tyr | Thr | Val |
| Gln 545 | Phe | Thr | Pro | Leu | Asn 550 | Pro | Asp | Asp | Phe | Arg 555 | Pro | Gly | Leu | Lys 560 |
| Asp | Thr | Lys | Leu | Leu 565 | Lys | Thr | Leu | Ala | Ile 570 | Gly | Asp | Thr | Ile | Thr 575 | Ser |
| Gln | Glu | Leu | Leu 580 | Ala | Gln | Ala | Gln | Ser 585 | Ile | Leu | Asn | Lys | Asn 590 | His | Pro |
| Gly | Tyr | Thr 595 | Ile | Tyr | Glu | Arg | Asp 600 | Ser | Ser | Ile | Val | Thr 605 | His | Asp | Asn |
| Asp | Ile 610 | Phe | Arg | Thr | Ile | Leu 615 | Pro | Met | Asp | Gln | Glu 620 | Phe | Thr | Tyr | Arg |
| Val 625 | Lys | Asn | Arg | Glu | Gln 630 | Ala | Tyr | Arg | Ile | Asn 635 | Lys | Lys | Ser | Gly | Leu 640 |
| Asn | Glu | Glu | Ile | Asn 645 | Asn | Thr | Asp | Leu | Ile 650 | Ser | Glu | Lys | Tyr | Tyr 655 | Val |
| Leu | Lys | Lys | Gly 660 | Glu | Lys | Pro | Tyr | Asp 665 | Pro | Phe | Asp | Arg | Ser 670 | His | Leu |
| Lys | Leu | Phe 675 | Thr | Ile | Lys | Tyr | Val 680 | Asp | Val | Asp | Thr | Asn 685 | Glu | Leu | Leu |
| Lys | Ser 690 | Glu | Gln | Leu | Leu | Thr 695 | Ala | Ser | Glu | Arg | Asn 700 | Leu | Asp | Phe | Arg |
| Asp 705 | Leu | Tyr | Asp | Pro | Arg 710 | Asp | Lys | Ala | Lys | Leu 715 | Leu | Tyr | Asn | Asn | Leu 720 |
| Asp | Ala | Phe | Gly | Ile 725 | Met | Asp | Tyr | Thr | Leu 730 | Thr | Gly | Lys | Val | Glu 735 | Asp |
| Asn | His | Asp | Asp 740 | Thr | Asn | Arg | Ile | Ile 745 | Thr | Val | Tyr | Met | Gly 750 | Lys | Arg |
| Pro | Glu | Gly 755 | Glu | Asn | Ala | Ser | Tyr 760 | His | Leu | Ala | Tyr | Asp 765 | Ala | Asp | Arg |
| Tyr | Thr 770 | Glu | Glu | Glu | Arg | Glu 775 | Val | Tyr | Ser | Tyr | Leu 780 | Arg | Tyr | Thr | Gly |
| Thr 785 | Pro | Ile | Pro | Asp | Asn 790 | Pro | Asn | Asp | Lys | Asn 795 | Asn | Ser | Gln | Leu | Val 800 |

Val Ser Val Ala Gly Thr Val Glu Gly Thr Asn Gln Asp Ile Ser Leu
              805                 810                 815

Lys Phe Phe Glu Ile Asp Leu Thr Ser Arg Pro Ala His Gly Gly Lys
            820                 825                 830

Thr Glu Gln Gly Leu Ser Pro Lys Ser Lys Pro Phe Ala Thr Asp Ser
            835                 840                 845

Gly Ala Met Ser His Lys Leu Glu Lys Ala Asp Leu Leu Lys Ala Ile
            850                 855                 860

Gln Glu Gln Leu Ile Ala Asn Val His Ser Asn Asp Asp Tyr Phe Glu
865                 870                 875                 880

Val Ile Asp Phe Ala Ser Asp Ala Thr Ile Thr Asp Arg Asn Gly Lys
                    885                 890                 895

Val Tyr Phe Ala Asp Lys Asp Gly Ser Val Thr Leu Pro Thr Gln Pro
                900                 905                 910

Val Gln Glu Phe Leu Leu Ser Gly His Val Arg Val Arg Tyr Lys Glu
            915                 920                 925

Lys Pro Ile Gln Asn Gln Ala Lys Ser Val Asp Val Glu Tyr Thr Val
            930                 935                 940

Gln Phe Thr Pro Leu Asn Pro Asp Asp Asp Phe Arg Pro Gly Leu Lys
945                 950                 955                 960

Asp Thr Lys Leu Leu Lys Thr Leu Ala Ile Gly Asp Thr Ile Thr Ser
                965                 970                 975

Gln Glu Leu Leu Ala Gln Ala Gln Ser Ile Leu Asn Lys Asn His Pro
            980                 985                 990

Gly Tyr Thr Ile Tyr Glu Arg Asp Ser Ser Ile Val Thr His Asp Asn
            995                 1000                1005

Asp Ile Phe Arg Thr Ile Leu Pro Met Asp Gln Glu Phe Thr Tyr Arg
    1010                1015                1020

Val Lys Asn Arg Glu Gln Ala Tyr Arg Ile Asn Lys Lys Ser Gly Leu
1025                1030                1035                1040

Asn Glu Glu Ile Asn Asn Thr Asp Leu Ile Ser Glu Lys Tyr Tyr Val
                1045                1050                1055

Leu Lys Lys Gly Glu Lys Pro Tyr Asp Pro Phe Asp Arg Ser His Leu
            1060                1065                1070

Lys Leu Phe Thr Ile Lys Tyr Val Asp Val Asp Thr Asn Glu Leu Leu
            1075                1080                1085

Lys Ser Glu Gln Leu Leu Thr Ala Ser Glu Arg Asn Leu Asp Phe Arg
            1090                1095                1100

Asp Leu Tyr Asp Pro Arg Asp Lys Ala Lys Leu Leu Tyr Asn Asn Leu
1105                1110                1115                1120

Asp Ala Phe Gly Ile Met Asp Tyr Thr Leu Thr Gly Lys Val Glu Asp
                1125                1130                1135

Asn His Asp Asp Thr Asn Arg Ile Ile Thr Val Tyr Met Gly Lys Arg
            1140                1145                1150

Pro Glu Gly Glu Asn Ala Ser Tyr His Leu Ala Tyr Asp Lys Asp Arg
            1155                1160                1165

Tyr Thr Glu Glu Glu Arg Glu Val Tyr Ser Tyr Leu Arg Tyr Thr Gly
        1170                1175                1180

Thr Pro Ile Pro Asp Asn Pro Asn Asp Lys
1185                1190

( 2 ) INFORMATION FOR SEQ ID NO:19:

( i ) SEQUENCE CHARACTERISTICS:
      ( A ) LENGTH: 2566 base pairs (B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:19:

| | | | | | | |
|---|---|---|---|---|---|---|
| CTGCAGCTAC | CTGATACCAG | GCATTTCCAA | CAAACATGGT | TAAGGCCAAA | CCAAAATCAC | 60 |
| TTTCTAGCGT | TGGCAAGAGA | CCTTCAAGCG | AGCGCAAGAC | CTTTATTGAA | GTTGCTTGTC | 120 |
| GACATAAAAA | TGCTGTTTGG | GTTGTGCTGA | TAGGCAAAAT | GACCTCAAGC | CCTGCAATCA | 180 |
| TCTGCTGGAG | CAACTCAACT | AAGTCAGCTG | GTAAAACCTG | CTGATGATTG | AGGTAAATAA | 240 |
| ACTGAGAAGT | CTCAAACAGC | TGAGGGGGAT | TGCCCTGATG | ATCAAGCAAA | TACCGCTGCC | 300 |
| AAGGTGACCC | TAGCGGCTGC | AAGACCTCAT | ATTGACCCAA | CCCCACCTCA | AGTAATAAGC | 360 |
| GCTCTTTTTC | GGATAAACAT | GATTTGGGAA | AATGCACATA | TTGGTCCCCT | TCTTTGACAC | 420 |
| TCACCCACTC | TTTATCTCCT | AACGGATGAG | GGCCTACTTG | CATCTCTGGA | AAATAGTCTT | 480 |
| TTAGCTCCAT | AGCCATTCCT | TTCATGACGG | TCTTTAAACC | ATTATAACAC | ATGACTCTTT | 540 |
| ATCACACAGT | TCAGTTTGTT | GTCAGCACGA | TTTTGTATTT | TCTGCCTTTT | TAATCATTAA | 600 |
| AACTAAATAA | GGGTTATTCA | TTTTTAGCAA | GAACATTCAA | TTAAATAGCT | ATTTATCGGA | 660 |
| ATATTAATTT | ATGTTTATGC | TAAAAAAGGT | ATTATTTACC | TTTTTTCATT | GTCATTAAAA | 720 |
| TATCATTTTA | AAAAAATCAA | TAGGTTTTTA | TTTGTGTCTT | TAAAACCATT | ATGTTATTCT | 780 |
| AATAATGGGG | ATTGAAACTT | AACTTTTAGG | AGGTTTCTAT | GAAAATTAC | TTATCTTTTG | 840 |
| GGATGTTTGC | ACTGCTGTTT | GCACTAACAT | TTGGAACAGT | CAATTCTGTC | CAAGCTATTG | 900 |
| CTGGACCTGA | GTGGCTGCTA | GACCGTCCAT | CTGTCAACAA | CAGCCAATTA | GTTGTTAGCG | 960 |
| TTGCTGGTAC | TGTTGAGGGG | ACGAATCAAG | ACATTAGTCT | TAAATTTTTT | GAAATCGATC | 1020 |
| TAACATCACG | ACCTGCTCAT | AGGAAAGACA | GAGCAAGGCT | TAAGTCCAAA | ATCAAAACCA | 1080 |
| TTTGCTACTG | ATAGTGGCGC | GATGTCACAT | AAACTTGAGA | AAGCTGACTT | ACTAAAGGCT | 1140 |
| ATTCAAGAAC | AATTGATCGC | TAACGTCCAC | AGTAACGACG | ACTACTTTGA | GGTCATTGAT | 1200 |
| TTTGCAAGCG | ATGCAACCAT | TACTGATCGA | AACGGCAAGG | TCTACTTTGC | TGACAAAGAT | 1260 |
| GGTTCGGTAA | CCTTGCCGAC | CCAACCTGTC | CAAGAATTTT | TGCTAAGCGG | ACATGTGCGC | 1320 |
| GTTAGACCAT | ATAAAGAAAA | ACCAATACAA | AACCAAGCGA | AATCTGTTGA | TGTGGAATAT | 1380 |
| ACTGTACAGT | TTACTCCCTT | AAACCCTGAT | GACGATTTCA | GACCAGGTCT | CAAAGATACT | 1440 |
| AAGCTATTGA | AAACACTAGC | TATCGGTGAC | ACCATCACAT | CTCAAGAATT | ACTAGCTCAA | 1500 |
| GCACAAAGCA | TTTTAAACAA | AAACCACCCA | GGCTATACGA | TTTATGAACG | TGACTCCTCA | 1560 |
| ATCGTCACTC | ATGACAATGA | CATTTTCCGT | ACGATTTTAC | CAATGGATCA | AGAGTTTACT | 1620 |
| TACCGTGTTA | AAAATCGGGA | ACAAGCTTAT | AGGATCAATA | AAAAATCTGG | TCTGAATGAA | 1680 |
| GAAATAAACA | ACACTGACCT | GATCTCTGAG | AAATATTACG | TCCTTAAAAA | AGGGGAAAAG | 1740 |
| CCGTATGATC | CCTTTGATCG | CAGTCACTTG | AAACTGTTCA | CCATCAAATA | CGTTGATGTC | 1800 |
| GATACCAACG | AATTGCTAAA | AAGTGAGCAG | CTCTTAACAG | CTAGCGAACG | TAACTTAGAC | 1860 |
| TTCAGAGATT | TATACGATCC | TCGTGATAAG | GCTAAACTAC | TCTACAACAA | TCTCGATGCT | 1920 |
| TTTGGTATTA | TGGACTATAC | CTTAACTGGA | AAAGTAGAGG | ATAATCACGA | TGACACCAAC | 1980 |
| CGTATCATAA | CCGTTTATAT | GGGCAAGCGA | CCCGAAGGAG | AGAATGCTAG | CTATCATTTA | 2040 |
| GCCTATGATA | AAGATCGTTA | TACCGAAGAA | GAACGAGAAG | TTTACAGCTA | CCTGCGTTAT | 2100 |
| ACAGGGACAC | CTATACCTGA | TAACCCTAAC | GACAAATAAC | CACGGTCTTC | TAAAACGATG | 2160 |

-continued

| | | | | | |
|---|---|---|---|---|---|
| AGATTAACTG | ACAAAAAAAG | CAAGCAACAT | GCTATCAACA | GTTGCTTGCT | TTTTTCTAAC | 2220 |
| CTCTTAGTTG | TAGAGACTAG | TGACATTTCG | TGTCTAAAAT | AATCGTAACT | GGTCCATCAT | 2280 |
| TGATGAGACT | AACCTGCATA | TCTGCCCCAA | AAACGCCACG | CTCAACTGGC | ACAAAATCTG | 2340 |
| CCAATTGTTC | ATTAAAGCGA | TCATAAAACT | GGCTAGCCAT | ATCAGCTTTG | CAGCTCCTGT | 2400 |
| AAAGGCTGGG | CGATTTCCCT | TTTTGGTGTC | AGCATAAAGG | GTAAATTGCG | ACACAGATAA | 2460 |
| GATACTACCC | TTGATGTCTT | GGATAGACTG | ATTCATCTTG | CCATCAGCAT | CTGAAAAAAT | 2520 |
| GCGCATGTTG | ACTATTTTTG | CACAGCGTAA | GCCAAATCTT | CTGCAG | | 2566 |

( 2 ) INFORMATION FOR SEQ ID NO:20:

( i ) SEQUENCE CHARACTERISTICS:
        ( A ) LENGTH: 1143 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

| | | | | | |
|---|---|---|---|---|---|
| ATGAAAACTG | AAGAAGGTAA | ACTGGTAATC | TGGATTAACG | GCGATAAAGG | CTATAACGGT | 60 |
| CTCGCTGAAG | TCGGTAAGAA | ATTCGAGAAA | GATACCGGAA | TTAAAGTCAC | CGTTGAGCAT | 120 |
| CCGGATAAAC | TGGAAGAGAA | ATTCCCACAG | GTTGCGGCAA | CTGGCGATGG | CCCTGACATT | 180 |
| ATCTTCTGGG | CACACGACCG | CTTTGGTGGC | TACGCTCAAT | CTGGCCTGTT | GGCTGAAATC | 240 |
| ACCCCGGACA | AAGCGTTCCA | GGACAAGCTG | TATCCGTTTA | CCTGGGATGC | CGTACGTTAC | 300 |
| AACGGCAAGC | TGATTGCTTA | CCCGATCGCT | GTTGAAGCGT | TATCGCTGAT | TTATAACAAA | 360 |
| GATCTGCTGC | CGAACCCGCC | AAAAACCTGG | GAAGAGATCC | CGGCGCTGGA | TAAAGAACTG | 420 |
| AAAGCGAAAG | GTAAGAGCGC | GCTGATGTTC | AACCTGCAAG | AACCGTACTT | CACCTGGCCG | 480 |
| CTGATTGCTG | CTGACGGGGG | TTATGCGTTC | AAGTATGAAA | ACGGCAAGTA | CGACATTAAA | 540 |
| GACGTGGGCG | TGGATAACGC | TGGCGCGAAA | GCGGGTCTGA | CCTTCCTGGT | TGACCTGATT | 600 |
| AAAAACAAAC | ACATGAATGC | AGACACCGAT | TACTCCATCG | CAGAAGCTGC | CTTTAATAAA | 660 |
| GGCGAAACAG | CGATGACCAT | CAACGGCCCG | TGGGCATGGT | CCAACATCGA | CACCAGCAAA | 720 |
| GTGAATTATG | GTGTAACGGT | ACTGCCGACC | TTCAAGGGTC | AACCATCCAA | ACCGTTCGTT | 780 |
| GGCGTGCTGA | GCGCAGGTAT | TAACGCCGCC | AGTCCGAACA | AAGAGCTGGC | GAAAGAGTTC | 840 |
| CTCGAAAACT | ATCTGCTGAC | TGATGAAGGT | CTGGAAGCGG | TTAATAAAGA | CAAACCGCTG | 900 |
| GGTGCCGTAG | CGCTGAAGTC | TTACGAGGAA | GAGTTGGCGA | AAGATCCACG | TATTGCCGCC | 960 |
| ACCATGGAAA | ACGCCCAGAA | AGGTGAAATC | ATGCCGAACA | TCCCGCAGAT | GTCCGCTTTC | 1020 |
| TGGTATGCCG | TGCGTACTGC | GGTGATCAAC | GCCGCCAGCG | GTCGTCAGAC | TGTCGATGAA | 1080 |
| GCCCTGAAAG | ACGCGCAGAC | TAATTCGAGC | TCGGTACCCG | GCCGGGATC | CATCGAGGGT | 1140 |
| AGG | | | | | | 1143 |

Other embodiments are within the following claims:

What is claimed is:

1. A plasminogen-binding fragment of streptokinase, wherein (a) said fragment lacks 1 to 24 amino-terminal amino acids;

(b) said fragment is catalytically active; and (c) the rate of in vitro degradation of said fragment in the presence of human plasminogen is at least 2 times slower compared to the rate of degradation of native streptokinase in the presence of human plasminogen, wherein the rate of degradation is measured by the appearance of plasmin cleavage products as detected by immunoblotting using anti-streptokinase antibodies, and (d) wherein said fragment further comprises at least one mutation in a potential plasmin cleavage site which renders said cleavage site resistant to cleavage by plasmin.

2. The fragment of claim 1, wherein said fragment comprises the amino acid sequence of (SEQ ID NO:4).

3. A polypeptide comprising a plasminogen-binding fragment of streptokinase, wherein (a) said fragment is catalytically active; and (b) the rate of in vitro degradation of said polypeptide in the presence of human plasminogen is at least two times slower compared to the rate of degradation of native streptokinase in the presence of human plasminogen, wherein the rate of degradation is measured by the appearance of plasmin cleavage products as detected by immunoblotting using anti-streptokinase antibodies, and (c) wherein said polypeptide further comprises at least one mutation in a potential plasmin cleavage site which renders said cleavage site resistant to cleavage by plasmin.

4. The polypeptide of claim 3, wherein said mutation is selected from the group consisting of R10A, K36A, R45A, K51A, K59A, K61A, K147A, K333, R232A, K257A, K298A, K309A, R234A, R363A, K386A, K372A, R388A, R394A, and R401A.

5. The polypeptide of claim 4, wherein said polypeptide comprises R10A, K36A, R45A, K51A and K59A (SEQ ID NO:17).

6. The polypeptide of claim 4, wherein said polypeptide comprises R10A, K36A, R45A, K51A, K59A and K386A (SEQ ID NO:18).

7. A compound comprising (a) a plasminogen-binding fragment of streptokinase and (b) a blocking group at the amino-terminus of said fragment, wherein (i) said compound is catalytically active; and (ii) the rate of in vitro degradation of said compound in the presence of human plasminogen is at least 2 times slower compared to the rate of degradation of native streptokinase in the presence of human plasminogen, wherein the rate of degradation is measured by the appearance of plasmin cleavage products as detected by immunoblotting using anti-streptokinase antibodies, and (iii) said blocking group is a non-peptide blocking group.

8. The compound of claim 7, wherein said blocking group is attached to the fragment by glycosylation or myristolization.

* * * * *